US011021479B2

(12) United States Patent
Kurz et al.

(10) Patent No.: US 11,021,479 B2
(45) Date of Patent: Jun. 1, 2021

(54) PYRIDOQUINAZOLINE DERIVATIVES USEFUL AS PROTEIN KINASE INHIBITORS

(71) Applicant: ONCOSTELLAE, S.L., a Coruña (ES)

(72) Inventors: Guido Kurz, Barcelona (ES); Juan Camacho Gómez, Navarra (ES)

(73) Assignee: ONCOSTELLAE, S.L., a Coruña (ES)

( * ) Notice: Subject to any disclaimer, the term of this patent is extended or adjusted under 35 U.S.C. 154(b) by 24 days.

(21) Appl. No.: 16/615,867

(22) PCT Filed: May 31, 2018

(86) PCT No.: PCT/ES2018/070396
§ 371 (c)(1),
(2) Date: Nov. 22, 2019

(87) PCT Pub. No.: WO2018/220252
PCT Pub. Date: Dec. 6, 2018

(65) Prior Publication Data
US 2020/0148676 A1    May 14, 2020

(30) Foreign Application Priority Data

Jun. 1, 2017 (ES) .............................. ES201730759

(51) Int. Cl.
*C07D 471/04* (2006.01)
*A61K 45/06* (2006.01)

(52) U.S. Cl.
CPC ............ *C07D 471/04* (2013.01); *A61K 45/06* (2013.01)

(58) Field of Classification Search
CPC .............................. C07D 471/04; A61K 45/06
USPC ......................................................... 514/267
See application file for complete search history.

(56) References Cited

U.S. PATENT DOCUMENTS

| 4,551,460 | A | 11/1985 | Tilley |
| 8,575,153 | B2 | 11/2013 | Kitamura et al. |
| 8,642,660 | B2 * | 2/2014 | Goldfarb ............... A61K 31/47 514/641 |
| 2017/0081322 | A1 | 3/2017 | Laiho et al. |

FOREIGN PATENT DOCUMENTS

| EP | 2 380 877 | 10/2011 |
| WO | WO 98/23617 | 6/1998 |
| WO | WO 2015/143293 | 9/2015 |

OTHER PUBLICATIONS

Mikhalev, A.I., et al., Synthesis, Anti-Inflammatory and Analgesic Activity of Pyrido[2,1-b] Quinazoline Derivatives, Pharmac. Chem. J., 29(2) (1995), 124-125.

Goedken, E.R., et al., Tricyclic Covalent Inhibitors Selectively Target Jak3 through an Active Site Thiol, J. Biol. Chem., 290(8) 2015, 4573-4589.
Roskoski, R., Classification of small molecule protein kinase inhibitors based upon the structures of their drug-enzyme complexes, Pharmacological Research 103 (2016) 26-48.
Sun, X., et al., The regulation and function of the NUAK family, Journal of Molecular Endocrinology (2013) 51,R15-R22.
Xu, T., et al, ARK5 promotes doxorubicin resistance in hepatocellular carcinoma via epithelial-mesenchymal transition, Cancer Letters (2016), doi: 0.1016/j.canlet.2016.04.026.
Cui, J., et al., Overexpression of ARK5 is associated with poor prognosis in hepatocellular carcinoma, Tumor Biol. 2013, doi: 10.1007/s13277-013-0735-x.
Liu, L., et al., Deregulated MYC expression induces dependence upon AMPK-related kinase 5, Nature 2012, 483, 608.
Li, X., et al., MYC-mediated synthetic lethality for treating tumors, Current Cancer Drug Targets 2015, 15, 99-115 (Abstract Only).
Aggarwal, B.B., et al., Singal Transducer and Activator of Transcription-3, Inflammation, and Cancer, Ann. N.Y. Acad. Sci. 1171: 59-76 (2009).
Jiang, J-J., et al., Advances in the Inhibitors of Janus Kinase, Med Chem, 2014, 4:8 540-548.
Dymock, B.W., et al., Selective JAK Inhibitors, Future Med Chem 2014, 6, 1439.
Ghoreschi, K., et al., Jakpot! New small molecules in autoimmune and inflammatory diseases, Experimental Dermatology, 2014, 23, 7-11.
Chiricozzi, A., et al., Tofacitinib for the treatment of moderate-to-severe psoriasis, Expert Rev. Clin. Immunol. (2015) doi: 10.1586/1744666X.2015.1013534.
Sandborn, W.J., et al., A Phase 2 Study of Tofacitinib, an Oral Janus Kinase Inhibitor, in Patients With Crohn's Disease, Clin. Gastroenterol Hepatol., Sep. 2014;12(9):1485-93.
Armstrong, A.W., et al., JAK Inhibitors: Treatment Efficacy and Safety Profile in Patients with Psoriasis J. of Immunology Res., vol. 2014, Article ID 283617, 7 pages.
Beattie, D., et al., TD-1473, a novel, potent, and orally administered, GI-targeted, pan-Janus kinase (JAK) inhibitor, Abstr. 11th Congress ECCO, P069, p. S123, (2016).
Vuitton, L., et al., Janus Kinase Inhibition with Tofacitinib: Changing the Face of Inflammatory Bowel Disease Treatment, Current Drugs Targets, 2013, 14, 1385-1391.
Yan Liang, et al., Therapeutic potential of tyrosine kinase 2 in autoimmunity, Expert Opin. Ther. Targets, (2014) 18(5):571-580.
Menet, C.J., Toward selective TYK2 inhibitors as therapeutic agents for the treatment of inflammatory diseases, Pharm. Pat. Anal. (2014) 3(4), 449-466.
Results of a structural search carried out by the Spanish Patent and Trademark Office in Priority application.

* cited by examiner

*Primary Examiner* — Niloofar Rahmani
(74) *Attorney, Agent, or Firm* — Tristan A. Fuierer; Olive Law Group, PLLC

(57) ABSTRACT

The present invention relates to novel 11-oxo-11H-pyrido[2,1-b]quinazoline-6-carboxamide derivatives as potent inhibitors of protein kinase, to pharmaceutical compositions containing them and to the use of said compounds for the manufacture of a drug for the treatment of diseases or pathological diseases that can be improved by inhibiting protein kinase.

15 Claims, No Drawings
Specification includes a Sequence Listing.

PYRIDOQUINAZOLINE DERIVATIVES USEFUL AS PROTEIN KINASE INHIBITORS

CROSS-REFERENCE TO RELATED APPLICATIONS

This application is filed under the provisions of 35 U.S.C. § 371 and claims the priority of International Patent Application No. PCT/ES2018/070396 filed on May 31, 2018 entitled "PYRIDOQUINAZOLINE DERIVATIVES USEFUL AS PROTEIN KINASE INHIBITORS" in the name of Guido KURZ, et al., which claims priority to Spanish Patent Application No. P201730759, filed on Jun. 1, 2017, both of which are hereby incorporated by reference herein in their entirety.

FIELD OF THE INVENTION

The present invention relates to novel 11-oxo-11H-pyrido[2,1-b]quinazoline-6-carboxamide derivatives conveniently substituted as potent inhibitors of at least one protein kinase, especially a kinase selected from the group consisting of AMPK-related kinase ARK5 and Janus kinase JAK3 and Janus kinase TYK2.

Other objectives of the present invention are to provide a procedure for preparing these compounds; pharmaceutical compositions comprising an effective amount of these compounds; the use of the compounds for manufacturing a medicament for the treatment of pathological conditions or diseases that can improve by inhibition of at least one kinase selected from ARK5, JAK3 and TYK2, such as autoimmune diseases including psoriasis, atopic dermatitis, rheumatoid arthritis, multiple sclerosis, alopecia areata, lupus, inflammatory bowel diseases including ulcerative colitis and Crohn's disease, cancer such as blood cancer, gastric cancer, colon cancer, colorectal cancer, liver cancer, lung cancer, pancreatic cancer, breast cancer, and other solid tumours, and others diseases such as asthma, chronic obstructive pulmonary disease (COPD), transplant rejection, haematological disease, uveitis, dry eye and allergic conjunctivitis, among others.

STATE OF THE ART

Protein kinases are enzymes that play key regulatory roles in nearly every aspect of cell biology. These enzymes participate in signal transduction modules that regulate apoptosis, cell cycle progression, cytoskeletal rearrangement, differentiation, development, the immune response, nervous system function and transcription. Protein kinases represent attractive drug targets because their dysregulation occurs in a variety of illnesses including cancer, diabetes autoimmune, cardiovascular, inflammatory and nervous disorders. (Roskoski, R., Classification of small molecule protein kinase inhibitors based upon the structures of their drug-enzyme complexes, Pharmacological Research 103 (2016) 26-48).

AMP-activated protein kinase (AMPK) is a protein kinase which has been found to be a master sensor and regulator of energy homeostasis. Its activity is regulated by increased intracellular AMP:ATP ratio in cells under metabolic stress (hypoxia, heat shock and ischemia).

Recently, twelve AMPK-related kinases (ARKs) have been identified and have shown great sequence homology to the catalytic domain of AMPK. One of these ARK is ARK5 (also known as NUAK1: novel (nua) kinase family (Sun, X et al, *The regulation and function of the NUAK family*, Journal of Molecular Endocrinology (2013) 51, R15-R22)), which may play a role in regulating tumor proliferation and survival through metabolic alteration. ARK5 is overexpressed in malignancies such as breast cancer, colorectal carcinoma, and hepatocellular carcinoma; patients with ARK5 overexpression often have poor prognosis. (Xu, T et al, *ARK5 promotes doxorubicin resistance in hepatocellular carcinoma via epithelial-mesenchymal transition*, Cancer Letters (2016), doi: 10.1016/j.canlet.2016.04.026 and references therein).

Particularly, there are studies showing that ARK5 is an independent prognostic factor for overall survival in patients with hepatocellular carcinoma (HCC). High expression of ARK5 in tumor is strongly correlated with tumor size, histological differentiation, and tumor-node-metastasis (TNM) stage. These findings suggest that ARK5 might be used as a new biomarker and a potential therapeutic target for HCC. (Cui, J et al, *Overexpression of ARK5 is associated with poor prognosis in hepatocellular carcinoma*, Tumor Biol. 2013, DOI 10.1007/513277-013-0735-x).

ARK5 was found to be specifically required for the viability of cells overexpressing MYC, an oncoprotein that contributes to the genesis of many human tumors (Liu et al, *Deregulated MYC expression induces dependence upon AMPK-related kinase 5*, Nature 2012, 483, 608). MYC function is closely associated with MYC levels, therefore ARK5 inhibition offers a therapeutic strategy to eliminate tumor cells that express deregulated MYC (Li et al, *MYC-mediated synthetic lethality for treating tumors*, Current Cancer Drug Targets 2015, 15, 99-115).

Currently it is known that Janus kinases (JAKs) are a family of intracellular, nonreceptor tyrosine kinases which are important signal transducers of many cytokines, growth factors and interferon. In recent years, it has been found that there is a significant enhancement in the expression of JAKs in cancer cells and cells transfected with oncogenes. It has also been described that the expression of JAKs has a close relationship with inflammation and autoimmune diseases and immune rejection of transplants. (Aggarwal, B B et al, *Signal Transducer and Activator of Transcription-3, Inflammation, and Cancer How Intimate Is the Relationship?* Ann. N.Y. Acad. Sci. 1171: 59-76 (2009) and references therein).

JAKs are a family of non-receptor tyrosine kinases that are relatively large molecules. There are four family members of JAKs: JAK1, JAK2, JAK3 and TYK2. JAK1, JAK2 and TYK2 exist in various tissues and cells, while JAK3 only exists in the marrow and lymphatic system. JAKs transmit extracellular stimuli through signals that are generated by the relevant receptors. Receptors and/or JAKs selectively activate signal transduction and signal transducer and activator of transcription (STAT) proteins by different phosphorylation sites. (Jiang J J et al, *Advances in the Inhibitors of Janus Kinase*, Med Chem, 2014, 4: 540-548 and references therein).

Selective inhibition of JAK kinases within the JAK family has been a desired goal of researchers in order to maximize efficacy while minimizing undesired off-target effects and to understand the role in disease of individual JAK isoforms and provide the most effective therapy for each indication. Delineation of the role of each kinase becomes possible with selective small-molecule inhibitors, but they must be selective within the kinome as well as the JAK family. This challenge is not trivial. The homology between the JAK kinases is high and the similarities in their ATP binding sites considerable. Despite these formidable obstacles, recent progress in the field has been impressive. There are now selective inhibitors for each of the JAK family members, with the expectation of seeing some of them entering the clinic in the near future (B. W. Dymock et al, *Selective JAK inhibitors*, Future Med Chem 2014, 6, 1439).

In the specific case of JAK3, it is a key cell signalling molecule in the immune response, which is specifically distributed in the lymphatic system; in which interleukin-2 (IL2) can activate JAK3 within a very short period of time. After a period of signal transduction, JAK3 can dephosphorylate and become inactive, so that signals generating quenching facilitate the next round of stimulus signal transmission. Thus, the inhibition of JAK3 activity will prevent side effects caused by damage to other tissues. (Jiang J J J et al, *Advances in the Inhibitors of Janus Kinase*, Med Chem, 2014, 4: 540-548 and references therein).

Currently, several JAK inhibitors small molecules have been developed with promising results. One of them, Tofacitinib, is a potent inhibitor of JAK3 and JAK1 with some activity against JAK2. It has been approved in several countries for the treatment of arthritis rheumatoid (RA), and is in advanced clinical phases for the treatment of patients with moderate-to-severe psoriasis. (Ghoreschi, K et al, Jakpot! *New small molecules in autoimmune and inflammatory diseases*, Experimental Dermatology, 2014, 23, 7-11) y (Chiricozzi A et al, *Tofacitinib for the treatment of moderate-to-severe psoriasis*, Expert Rev. Clin. Immunol. Early online, 1-13 (2015)).

Tofacitinib is also being investigated for the treatment of Crohn's disease, an inflammatory disease of the small intestine and colon characterized by alternating periods of relapse and remission, in patients with moderate-to-severe disease, although there were no significant differences in the percentage of patients with moderate-to-severe disease who achieved clinical responses after 4 weeks' administration of Tofacitinib or placebo. Therefore, additional studies are needed to determine whether Tofacitinib is effective for the treatment of Crohn's disease. (Sandborn, W et al, *A Phase 2 Study of Tofacitinib, an Oral Janus Kinase Inhibitor, in Patients with Crohn's Disease*, Current, Clin Gastroenterol Hepatol. 2014 September; 12(9):1485-93).

Others JAKs inhibitors are in clinical phases for the treatment of psoriasis and RA, among others conditions. One of them is the ASP015K (peficitinib), a selective JAK3 inhibitor, which is undergoing investigation for the treatment of moderate-to-severe psoriasis. (Armstrong A W, *JAK Inhibitors: Treatment Efficacy and Safety Profile in Patients with Psoriasis, Journal of Immunology Research*, Volume 2014, Article ID 283617, 7 pages). Additionally, others selective JAK3 inhibitors, such as VX-509 (decernotinib) are known. Among these VX-509 is in clinical phase for the treatment of RA, and R348 is in clinical phase for the treatment of lupus erythematosus. (Ghoreschi, K et al, *Jakpot! New small molecules in autoimmune and inflammatory diseases*, Experimental Dermatology, 2014, 23, 7-11) y (Chiricozzi A et al, Tofacitinib for the treatment of moderate-to-severe psoriasis, Expert Rev. Clin. Immunol. Early online, 1-13 (2015)).

TD-1473 is another potent JAK1, JAK2, JAK3, and TYK2 inhibitor at the human JAK kinase domains, which is considered a novel pan-JAK inhibitor, designed to inhibit JAK in the gastro intestinal (GI) tract upon oral dosing. The compound has demonstrated a favourable safety and tolerability profile in the initial clinical trial in healthy volunteers, so is has planned phase 1b trial in patients, in order to develop a treatment for ulcerative colitis and other inflammatory intestinal diseases. (Beattie D et al, *TD-1473, a novel, potent, and orally administered, GI-targeted, pan-Janus kinase (JAK) inhibitor*, Theravance Biopharma, South San Francisco, Poster presentations: Basic science (2016)).

In relation to the inflammatory bowel diseases (IBD), which are considered chronic and disabling conditions, and enclose two major forms of intestinal inflammation: ulcerative colitis and Crohn's disease, there is clinical evidence of Tofacitinib efficacy for ulcerative colitis (UC). (Vuitton, L et al, *Janus Kinase Inhibition with Tofacitinib: Changing the Face of Inflammatory Bowel Disease Treatment*, Current Drugs Targets, 2013, 14, 1385-1391).

Tofacitinib is also being investigated for the treatment of Crohn's disease, an inflammatory disease of the small intestine and colon characterized by alternating periods of relapse and remission, in patients with moderate-to-severe disease, although there were no significant differences in the percentage of patients with moderate-to-severe disease who achieved clinical responses after 4 weeks' administration of Tofacitinib or placebo. Therefore, additional studies are needed to determine whether Tofacitinib is effective for the treatment of Crohn's disease. (Sandborn, W et al, *A Phase 2 Study of Tofacitinib, an Oral Janus Kinase Inhibitor, in Patients with Crohn's Disease*, Current, Clin Gastroenterol Hepatol. 2014 September; 12(9):1485-93).

Accordingly, it is expected that inhibition of JAK3 could lead to the prevention and treatment of diseases including ulcerative colitis, Crohn's disease, asthma, allergic rhinitis, atopic dermatitis, contact dermatitis, urticaria, eczema, psoriasis, allergic conjunctivitis and uveitis, among others. (EP2380877 and references therein).

On the other hand, TYK2 enzyme has demonstrated an important role for signalling transduction in response to a wide variety of cytokines, including type I IFNs, IL-6, IL-10, IL-12 and IL-23. An appropriate expression of TYK2-mediated signalling might be essential for maintaining normal immune responses although in pathological conditions they promote the production of autoimmune-associated components, which are implicated in the pathogenesis of autoimmune diseases, such as rheumatoid arthritis, systemic lupus erythematosus, multiple sclerosis. Aberrant expression of TYK2 has been observed in many autoimmune conditions. (Yan Liang et al, *Therapeutic potential of tyrosine kinase 2 in autoimmunity*, Expert Opin. Ther. Targets (2014) 18(5):571-580). There are data supporting the idea of selective TYK2 inhibitors may be potential new therapies for the treatment of psoriasis and IBD without undesired broad immunosuppression. (Dymock B W et al, *Selective JAK inhibitors*, Future Med. Chem. (2014) 6(12), 1439-1471).

Despite the high level of interest in selective JAK inhibitors and their therapeutic potential, TYK2 remains the least explored member of this family. Only few disclosures claiming selective TYK2 inhibitors have been published to date and no TYK2-selective inhibitors are known to be in clinical trial. The only molecule claiming TYK2 inhibition currently in a clinical trial is a compound from Pfizer: pan-inhibitor PF-06263726 (topical, psoriasis). (Menet C J, *Toward selective TYK2 inhibitors as therapeutic agents for the treatment of inflammatory diseases*, Pharm. Pat. Anal. (2014) 3(4), 449-466).

Taking the above into account, most of the JAK inhibitors developed so far are selective for others kinases, but, as mentioned above, do not discriminate well among the JAK family members. Such promiscuity in inhibition often leads to concerns about toxicity and unacceptable side effects; it seems that the toxicity of the JAK inhibitors is limited although their long-term toxicity has not been fully determined. Therefore, the generation of highly selective inhibitors, with no off-target activity against other JAKs, may result in increased efficacy and safety. (Ghreschi K, et al, *Jakpot! New small molecules in autoimmune and inflammatory diseases*, Experimental Dermatology, 2014, 23, 7-11). Particularly, in the case of JAK2, due to its role in several physiological essential processes, such as erythropoiesis and neutrophil functions, to avoid its inhibition is particularly desirable. (Goedken E R et al, *Tricyclic Covalent Inhibitors Selectively Target Jak3 through an Active Site Thiol*, THE JOURNAL OF BIOLOGICAL CHEMISTRY VOL. 290, NO. 8, pp. 4573-4589, Feb. 20, 2015).

The authors of the present invention have developed new 11-oxo-11H-pyrido[2,1-b]quinazoline-6-carboxamide derivatives as potent and selective inhibitors of protein kinases, specifically of at least one enzyme selected from ARK5, JAK3 and TYK2.

SUMMARY OF THE INVENTION

In one of its aspects (aspect 1), the present invention refers to novel 11-oxo-11H-pyrido[2,1-b]quinazoline-6-carboxamide derivatives of formula (I):

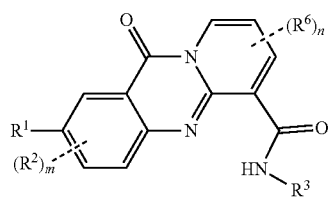

wherein:
$R^1$ represents a group selected from:
   a) $C_3$-$C_6$ cycloalkyl optionally substituted by a group selected from halogen atom, linear or branched $C_1$-$C_6$ alkyl and linear or branched $C_1$-$C_4$ alkoxy,
   b) phenyl optionally substituted by a group selected from halogen atom and linear or branched $C_1$-$C_6$ alkyl,
   c) $C_4$-$C_6$ heterocyclic ring containing 1 or 2 heteroatoms selected from N, O and S and which is optionally substituted by a group selected from halogen atom, linear or branched $C_1$-$C_6$ alkyl and linear or branched $C_1$-$C_4$ alkoxy,
   d) fluorine or bromine atom,
   e) cyano group,
   f) linear or branched $C_1$-$C_3$ alkoxy optionally substituted by 1, 2 or 3 halogen atoms.
   g) linear or branched $C_1$-$C_6$ alkyl optionally substituted by 1, 2 or 3 halogen atoms.
   h) —OH
$R^2$ and $R^6$ independently represent a group selected from:
   a) halogen atom,
   b) linear or branched $C_1$-$C_6$ alkyl,
   c) linear or branched $C_1$-$C_6$ haloalkyl,
   d) $C_3$-$C_6$ cycloalkyl optionally substituted by a group selected from halogen atom, linear or branched $C_1$-$C_3$ alkyl and linear or branched $C_1$-$C_2$ alkoxy,
   m and n are integers independently selected from 0 and 1,
$R^3$ represents a 5- to 10-membered, saturated, cycle optionally containing 1 or 2 heteroatoms selected from N and O, which is optionally substituted by 1, 2 or 3 groups selected from halogen atoms, linear or branched $C_1$-$C_6$ alkyl, linear or branched $C_1$-$C_6$ alkoxy, —OH and —$NR^4R^5$,
$R^4$ and $R^5$ represent independently a group selected from hydrogen atom, $C_3$-$C_4$ cycloalkyl group and linear or branched $C_1$-$C_4$ alkyl,
with the proviso that the compound of formula:

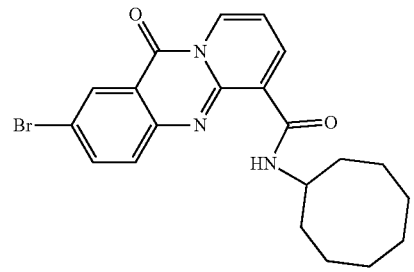 [SMILES: O=C(NC1CCCCCCC1)c1cccn2c(=O)c3cc(Br)ccc3nc12]

is excluded,
and pharmaceutically acceptable salts thereof.

In a second aspect, the present invention relates to processes for the preparation of the compounds of aspect 1.

In a third aspect the present invention relates to pharmaceutical compositions comprising a compound of aspect 1 and a pharmaceutical aspect diluent or carrier.

In a fourth aspect the present invention relates to pharmaceutical compositions according to the third aspect described above which further comprise a therapeutically effective amount of a therapeutic agent selected from agent useful for the treatment of autoimmune diseases including psoriasis, atopic dermatitis, rheumatoid arthritis, multiple sclerosis, alopecia areata, lupus, inflammatory bowel diseases including ulcerative colitis and Crohn's disease, cancers such as blood cancer, gastric cancer, colon cancer, colorectal cancer, liver cancer, lung cancer, pancreatic cancer, breast cancer, and other solid tumours, and others diseases such as asthma, chronic obstructive pulmonary disease (COPD), transplant rejection, haematological disease, uveitis, dry eye and allergic conjunctivitis, among others.

In a fifth aspect the present invention relates to the use of the compound of aspect 1 in the manufacture of a medicament for the treatment of a disease or pathological condition that can be ameliorated by inhibition of at least one enzyme selected from ARK5, JAK3 and TYK2, such as autoimmune diseases including psoriasis, atopic dermatitis, rheumatoid arthritis, multiple sclerosis, alopecia areata, lupus, inflammatory bowel diseases including ulcerative colitis and Crohn's disease, cancer such as blood, gastric, colon, colorectal, liver, lung, pancreatic, breast, and other solid tumours, and others diseases such as asthma, chronic obstructive pulmonary disease (COPD), transplant rejection, haematological disease, uveitis, dry eyes and allergic conjunctivitis, among others.

In a sixth aspect the present invention relates to methods for the treatment of diseases that can be ameliorated by inhibition of at least one enzyme selected from ARK5, JAK3 and TYK2 by administration of the compounds of the first aspect or pharmaceutical compositions of the second or third aspects described above to a subject in need of said treatment; the diseases are selected from autoimmune diseases including psoriasis, atopic dermatitis, rheumatoid arthritis, multiple sclerosis, alopecia areata, lupus, inflammatory bowel diseases including ulcerative colitis and Crohn's disease, cancer such as blood cancer, gastric cancer, colon cancer, colorectal cancer, liver cancer, lung cancer, pancreatic cancer, breast cancer, and other solid tumours, and others diseases such as asthma, chronic obstructive pulmonary disease (COPD), transplant rejection, haematological disease, uveitis, dry eye and allergic conjunctivitis, among others.

In a seventh aspect the present invention relates to a combination product of the compound of the first aspect described above with one more therapeutic agent known to be useful in the treatment of diseases selected from such as autoimmune diseases including psoriasis, atopic dermatitis, rheumatoid arthritis, multiple sclerosis, alopecia areata, lupus, inflammatory bowel diseases including ulcerative colitis and Crohn's disease, cancer such as blood cancer, gastric cancer, colon cancer, colorectal cancer, liver cancer, lung cancer, pancreatic cancer, breast, and other solid tumours, and others diseases such as asthma, chronic obstructive pulmonary disease (COPD), transplant rejection, haematological disease, uveitis, dry eye and allergic conjunctivitis, among others.

In an eighth aspect the present invention relates to the compound of aspect 1 for use in the treatment of a disease or pathological condition that can be ameliorated by inhibition of at least one enzyme selected from ARK5, JAK3 and TYK2, such as autoimmune diseases including psoriasis, atopic dermatitis, rheumatoid arthritis, multiple sclerosis, alopecia areata, lupus, inflammatory bowel diseases including ulcerative colitis and Crohn's disease, cancer such as blood, gastric, colon, colorectal, liver, lung, pancreatic, breast, and other solid tumours, and others diseases such as asthma, chronic obstructive pulmonary disease (COPD), transplant rejection, haematological disease, uveitis, dry eye and allergic conjunctivitis, among others.

As it is said before, the 11-oxo-11H-pyrido[2,1-b]quinazoline-6-carboxamide derivatives of the invention are useful in the treatment or prevention of diseases known to be susceptible to amelioration by treatment with inhibitors of at least one enzyme kinases selected from ARK5, JAK3 and TYK2 such as autoimmune diseases including psoriasis, atopic dermatitis, rheumatoid arthritis, multiple sclerosis, alopecia areata, lupus, inflammatory bowel diseases including ulcerative colitis and Crohn's disease, cancer such as blood, gastric, colon, colorectal, liver, lung, pancreatic, breast, and other solid tumours, and others diseases such as asthma, chronic obstructive pulmonary disease (COPD), transplant rejection, haematological disease, uveitis, dry eye and allergic conjunctivitis, among others. In a preferred embodiment, the compounds of formula (I), due to their low to moderate systemic exposure after oral administration and consequently a lower risk of causing side effects, are especially suited for the topical/local treatment of diseases such as, for example, psoriasis, atopic dermatitis, alopecia areata, inflammatory bowel diseases including ulcerative colitis and Crohn's disease, asthma, chronic obstructive pulmonary disease (COPD), uveitis, dry eye and allergic conjunctivitis.

Accordingly, the derivatives of the present invention and pharmaceutically acceptable salts thereof, and pharmaceutical compositions comprising such compounds and/or salts thereof, may be used in a method of treatment of pathological conditions or disease of human body which comprises administering to a subject in need of said treatment, an effective amount of the 11-oxo-11H-pyrido[2,1-b]quinazoline-6-carboxamide derivative of the invention or a pharmaceutically acceptable salt thereof.

As used herein, the term $C_a$-$C_b$ cycloalkyl embraces hydrocarbon cyclic groups having a to b carbon atoms. Such cycloalkyl groups include, for example, cyclopropyl, cyclobutyl, cyclopentyl and cyclohexyl.

As used herein, the term $C_a$-$C_b$ alkyl includes linear or branched hydrocarbon radicals, having from a to b carbon atoms. Preferred radicals include 1 to 4 carbon atoms. Examples of linear or branched alky groups are methyl, ethyl, n-propyl, iso-propyl, n-butyl, i-butyl, sec-butyl, tert-buty, pentyl and hexyl.

As used herein, the term linear or branched $C_a$-$C_b$ alkoxy is used to designate radicals which contain linear or branched $C_a$-$C_b$ alkyl radicals linked to an oxygen atom ($C_xH_{2x-1}$—O—). Preferred alkoxy radicals include, for example, methoxy, ethoxy, n-propoxy, i-propoxy.

As used herein, the term $C_a$-$C_b$ heterocyclic ring embraces a saturated or unsaturated ring having a to b carbon atoms and at least a heteroatom selected from N, O and S forming part of the ring. Such heterocyclic ring includes, for example, pyridinyl, pyrimidinyl, piperazinyl, furyl, thienyl, piperazinyl, morpholinyl. Preferred radicals are optionally substituted pyridinyl, piperazinyl and morpholinyl group. Said heterocyclic rings are optionally substituted by 1, 2 or 3 substituents selected from halogen atom, $C_1$-$C_6$ alkyl linear or branched and $C_1$-$C_4$ alkoxy linear or branched. The substituents of the heterocyclic ring may be replacing a hydrogen atom of any of the carbon atoms in the ring or a hydrogen atom of any of the nitrogen atoms in the ring.

As used herein, the term halogen atom includes chlorine, fluorine, bromine and iodine atoms, preferably fluorine, chlorine and bromine atoms. The term halo, when used as a prefix, has the same meaning.

As used herein, the term a 5- to 10-membered, saturated, cycle embraces ring systems of 5- to 10 members containing carbon atoms and optionally 1 or 2 heteroatoms selected from N and O. Said ring systems may be monocyclic or polycyclic and the polycyclic ring system include systems with fused rings (i.e. rings sharing two ring atoms), bridged rings (i.e. rings sharing more than two ring atoms) and spiranic systems (i.e. wherein two rings share only one ring atom) Said cycles include, by way of example, the following monocyclic ring systems: cyclopentyl, cyclohexyl, tetrahydropyranyl, tetrahydrofuranyl, and piperidinyl, and the following polycyclic bridged ring systems: bicyclo[2.2.1]heptanyl, bicyclo[2.2.2] octanyl 7-aza-bicyclo[2.2.1]heptanyl and adamantyl. Said cycles are optionally substituted by 1, 2 or 3 substituents selected from $C_1$-$C_6$ alkyl linear or branched, $C_1$-$C_6$ alkoxy linear or branched, —OH and amines. The substituents of the 5- to 10-membered cycle may be replacing a hydrogen atom of any of the carbon atoms in the cycle or a hydrogen atom of any of the nitrogen atoms in the cycle.

In an embodiment, the 5- to 10-membered, saturated, polycyclic ring systems comprise two or more fused or bridged rings each consisting of 3 to 7 atoms, wherein 1 or 2 atoms can be heteroatoms selected from N and O.

As used herein, some of the atoms, radicals, chains or cycles present in the general structures of the invention are "optionally substituted". This means that these atoms, radicals, chains or cycles can be either unsubstituted or substituted in any position by one or more, for example 1, 2, 3 or 4, substituents, whereby the hydrogen atoms bound to the unsubstituted atoms, radicals, chains or cycles are replaced by chemically acceptable atoms, radicals, chains or cycles. When two or more substituents are present, each substituent may be the same or different As used herein, the term pharmaceutically acceptable salt is used to designate salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium), alkali earth metal (e.g. calcium or magnesium) hydroxides, and organic bases, for example alkyl amines, arylalkyl amines and heterocyclic amines.

Other preferred salts according to the invention are quaternary ammonium compounds wherein an equivalent of an anion ($X^{-n}$) is associated with the positive charge of the N atom. $X^{-n}$ may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulfonate and p-toluenesulphonate. $X^{-n}$ is preferably an anion selected from chloride, bromide, iodide, sulphate, nitrate, acetate, maleate, oxalate, succinate or trifluoroacetate. More preferably, $X^-$ is chloride, bromide, trifluoroacetate or methanesulfonate.

According to one embodiment of the present invention in the compounds of formula (I), $R^1$ represents a group selected from:
- $C_3$-$C_6$ cycloalkyl optionally substituted by a group selected from halogen atom, linear or branched $C_1$-$C_6$ alkyl and linear or branched $C_1$-$C_4$ alkoxy,
- $C_5$-$C_6$ heterocyclic ring containing 1 or 2 heteroatoms selected from N and O and which is optionally substituted by a group selected from halogen atom, linear or branched $C_1$-$C_6$ alkyl and linear or branched $C_1$-$C_4$ alkoxy.
- linear or branched $C_1$-$C_3$ alkoxy.

In a preferred embodiment $R^1$ represents a group selected from:
- $C_3$-$C_4$ cycloalkyl optionally substituted by a group selected from linear or branched $C_1$-$C_6$ alkyl and linear or branched $C_1$-$C_4$ alkoxy,
- six-membered heterocyclic ring containing 1 or 2 heteroatoms selected from N and O and which is optionally substituted by a group selected from linear or branched $C_1$-$C_6$ alkyl and linear or branched $C_1$-$C_4$ alkoxy.
- methoxy group.

In a more preferred embodiment, $R^1$ represents cyclopropyl group optionally substituted by a group selected from linear or branched $C_1$-$C_6$ alkyl and linear or branched $C_1$-$C_4$ alkoxy.

According to another embodiment of the present invention in the compound of formula (I) m and n have a value of 0.

In an embodiment, $R^3$ represents a 5- to 10-membered saturated monocyclic ring system containing carbon atoms and optionally 1 or 2 heteroatoms selected from N and O.

According to another embodiment of the present invention in the compounds of formula (I), $R^3$ represents a 5- to 6-membered saturated cycle optionally containing one oxygen atom and which is optionally substituted by a group selected from linear or branched $C_1$-$C_6$ alkyl and —OH.

In a more preferred embodiment, $R^3$ represents a group selected from cyclopentyl and cyclohexyl group optionally substituted by one group selected from linear or branched $C_1$-$C_6$ alkyl and —OH.

According to another embodiment of the present invention in the compounds of formula (I), $R^4$ and $R^5$ represent a hydrogen atom.

According to one embodiment of the present invention in the compounds of formula (I), $R^1$ represents a group selected from, methoxy group, cyclopropyl group optionally substituted by a group selected from linear or branched $C_1$-$C_6$ alkyl and linear or branched $C_1$-$C_4$ alkoxy and six-membered heterocyclic ring containing 1 or 2 heteroatoms selected from N and O and which is optionally substituted by a group selected from linear or branched $C_1$-$C_6$ alkyl, m and n have a value of 0 and $R^3$ represents a group selected from cyclopentyl and cyclohexyl group optionally substituted by one group selected from linear or branched $C_1$-$C_6$ alkyl and —OH.

According to one embodiment of the present invention in the compounds of formula (I), $R^1$ represents a group selected from six-membered heterocyclic ring containing 1 or 2 heteroatoms selected from N and O and which is optionally substituted by a group selected from linear or branched $C_1$-$C_6$ alkyl, m and n have a value of 0, and $R^3$ represents a group selected from cyclopentyl and cyclohexyl group optionally substituted by one group selected from linear or branched $C_1$-$C_6$ alkyl and —OH.

According to one embodiment of the present invention in the compounds of formula (I), $R^1$ represents a cyclopropyl group optionally substituted by a group selected from linear or branched $C_1$-$C_3$ alkyl and linear or branched $C_1$-$C_2$ alkoxy, n and m have a value of zero and $R^3$ represents a cyclohexyl group optionally substituted by a group selected from linear or branched $C_1$-$C_3$ alkyl and —OH.

Particular individual compounds of the present invention include:
N-cyclohexyl-2-cyclopropyl-11-oxo-11H-pyrido[2,1-b]quinazoline-6-carboxamide
N-cyclopentyl-2-cyclopropyl-11-oxo-11H-pyrido[2,1-b]quinazoline-6-carboxamide
2-cyclopropyl-N-(1-methylpiperidin-4-yl)-11-oxo-11H-pyrido[2,1-b]quinazoline-6-carboxamide
2-cyclopropyl-11-oxo-N-(tetrahydro-2H-pyran-4-yl)-11H-pyrido[2,1-b]quinazoline-6-carboxamide
2-cyclopropyl-N-(3-methyltetrahydro-2H-pyran-4-yl)-11-oxo-11H-pyrido[2,1-b]quinazoline-6-carboxamide
2-cyclopropyl-N-((1R,4R)-4-hydroxy-4-methylcyclohexyl)-11-oxo-11H-pyrido[2,1-b]quinazoline-6-carboxamide
2-cyclopropyl-N-((1R,4R)-4-hydroxycyclohexyl)-11-oxo-11H-pyrido[2,1-b]quinazoline-6-carboxamide
2-cyclopropyl-N-(2-hydroxycyclohexyl)-11-oxo-11H-pyrido[2,1-b]quinazoline-6-carboxamide
2-cyclopropyl-N-((1R,2R)-2-hydroxycyclohexyl)-11-oxo-11H-pyrido[2,1-b]quinazoline-6-carboxamide
2-cyclopropyl-N-((1S,2R)-2-hydroxycyclohexyl)-11-oxo-11H-pyrido[2,1-b]quinazoline-6-carboxamide
2-cyclopropyl-N-((1R,2S)-2-hydroxycyclohexyl)-11-oxo-11H-pyrido[2,1-b]quinazoline-6-carboxamide
2-cyclopropyl-N-((1S,2S)-2-hydroxycyclohexyl)-11-oxo-11H-pyrido[2,1-b]quinazoline-6-carboxamide
N-((1R,4R)-4-aminocyclohexyl)-2-cyclopropyl-11-oxo-11H-pyrido[2,1-b]quinazoline-6-carboxamide
2-cyclopropyl-11-oxo-N-(tetrahydrofuran-3-yl)-11H-pyrido[2,1-b]quinazoline-6-carboxamide
2-cyclopropyl-N-(4,4-difluorocyclohexyl)-11-oxo-11H-pyrido[2,1-b]quinazoline-6-carboxamide
N-cyclohexyl-2-cyclopropyl-8-methyl-11-oxo-11H-pyrido[2,1-b]quinazoline-6-carboxamide N-(4,4-difluorocyclohexyl)-2-fluoro-8-methyl-11-oxo-11H-pyrido[2,1-b]quinazoline-6-carboxamide
N-cyclopentyl-2-hydroxy-11-oxo-11H-pyrido[2,1-b]quinazoline-6-carboxamide
N-cyclohexyl-2-hydroxy-11-oxo-11H-pyrido[2,1-b]quinazoline-6-carboxamide
N-cyclohexyl-2-methoxy-11-oxo-11H-pyrido[2,1-b]quinazoline-6-carboxamide
N-cyclohexyl-11-oxo-2-(trifluoromethoxy)-11H-pyrido[2,1-b]quinazoline-6-carboxamide
N-cyclohexyl-2-methyl-11-oxo-11H-pyrido[2,1-b]quinazoline-6-carboxamide
N-cyclohexyl-11-oxo-2-(trifluoromethyl)-11H-pyrido[2,1-b]quinazoline-6-carboxamide
N-cyclohexyl-2-fluoro-11-oxo-11H-pyrido[2,1-b]quinazoline-6-carboxamide
2-bromo-N-cyclopentyl-11-oxo-11H-pyrido[2,1-b]quinazoline-6-carboxamide
2-bromo-N-cyclohexyl-11-oxo-11H-pyrido[2,1-b]quinazoline-6-carboxamide
2-bromo-N-((1S,2R)-2-hydroxycyclohexyl)-11-oxo-11H-pyrido[2,1-b]quinazoline-6-carboxamide
N-cyclohexyl-11-oxo-2-phenyl-11H-pyrido[2,1-b]quinazoline-6-carboxamide
N-cyclohexyl-2-(4-fluorophenyl)-11-oxo-11H-pyrido[2,1-b]quinazoline-6-carboxamide
N-cyclohexyl-11-oxo-2-(thiophen-2-yl)-11H-pyrido[2,1-b]quinazoline-6-carboxamide
2-cyano-N-cyclohexyl-11-oxo-11H-pyrido[2,1-b]quinazoline-6-carboxamide
N-cyclopentyl-11-oxo-2-(pyridin-4-yl)-11H-pyrido[2,1-b]quinazoline-6-carboxamide
N-cyclohexyl-11-oxo-2-(pyridin-4-yl)-11H-pyrido[2,1-b]quinazoline-6-carboxamide
N-((1S,2R)-2-hydroxycyclohexyl)-11-oxo-2-(pyridin-4-yl)-11H-pyrido[2,1-b]quinazoline-6-carboxamide
N-cyclopentyl-2-(4-methylpiperazin-1-yl)-11-oxo-11H-pyrido[2,1-b]quinazoline-6-carboxamide
N-cyclohexyl-2-(4-methylpiperazin-1-yl)-11-oxo-11H-pyrido[2,1-b]quinazoline-6-carboxamide
N-((1S,2R)-2-hydroxycyclohexyl)-2-(4-methylpiperazin-1-yl)-11-oxo-11H-pyrido[2,1-b]quinazoline-6-carboxamide
N-cyclohexyl-2-morpholino-11-oxo-11H-pyrido[2,1-b]quinazoline-6-carboxamide.

The compounds of the present invention can be prepared by using the procedures described below. To facilitate the description of the procedures, concrete examples have been used but they do not restrict in any way the scope of the present invention. The synthesis of compound of formula (I) is outlined in scheme 1.

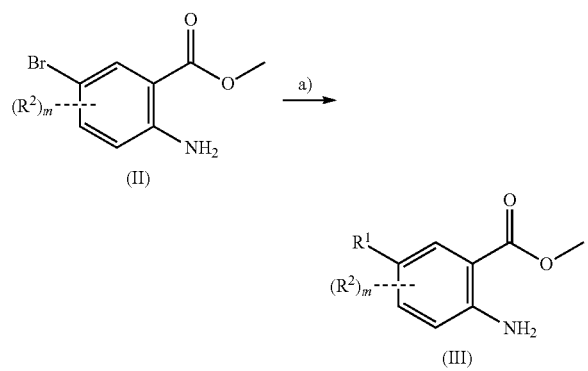

Scheme 1

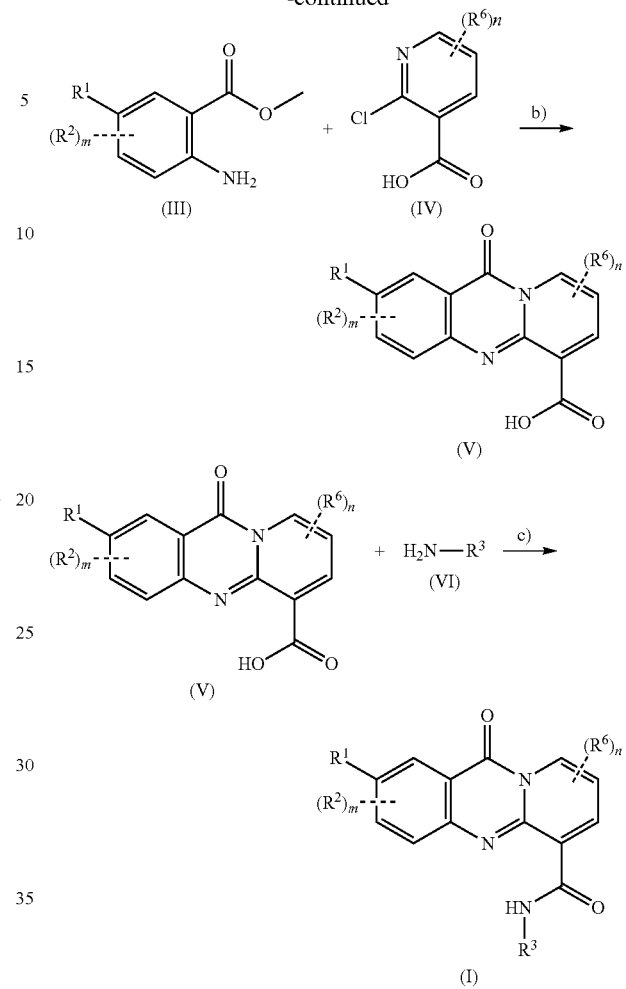

In the above scheme, compounds of formula (I) are compounds according to the present invention wherein $R^1$, $R^2$, $R^3$ and $R^6$ are as hereinabove defined.

Reagents and Conditions:
Step a) $R^1$—B(OH)$_2$, Pd-Cat.; or amines
Step b) HCl, Isopropanol 24 h, 100° C.
Step c) EDC, HOBt, EDIA, DMF, room temperature.

Derivatives of general formula (V) are prepared from commercially available optionally substituted 2-aminobenzic acids or ethyl or methyl optionally substituted 2-aminobenzoates or the correspondent optionally substituted amino-heteroaryl carboxylates (III) and optionally substituted 2-chloronicotinic acid or optionally substituted chlorheteroarylic acids (IV), according to Scheme 1. In some cases, that reagent (III) are not available, it can be obtained, for example, through the substitution of the bromide atom from the corresponding carboxylic acids or carboxylate derivatives of formula (II). The starting reagents (III) and (IV) are reacted by a cyclization reaction in acidic condition in isopropanol, dioxane or xylene at temperatures between 80° and 110° C. to provide acids of formula (V). The reaction of these acids with amines (VI) in polar aprotic solvents such as DCM, THF, Acetonitrile or DMF in the presence of coupling reagent such as HATU, EDC, HOBt or T3P and temperatures ranging from 0° C. to 80° C. provides compounds of formula (I), which are the object of the present invention.

Another way to obtain in certain positions substituted compounds of formula (I) is achieved, for example, through the nucleophilic substitution of brominated derivatives (VII) and (VIII) with amines or through the coupling reaction of these derivatives, for instance with aryl or heteroaryl boronic acids under Suzuki conditions according to scheme 2. Such compounds of formula (Ia) and (Ib) are particular cases of the present invention.

Scheme 2

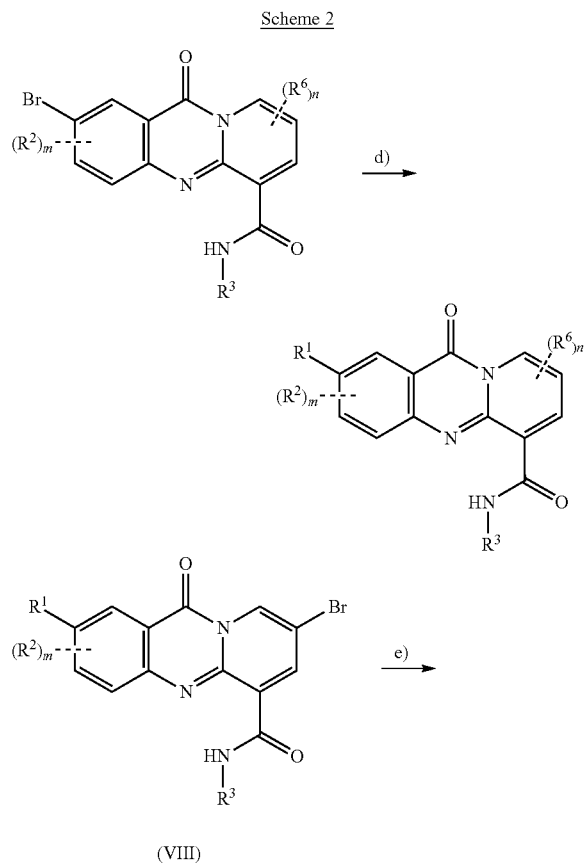

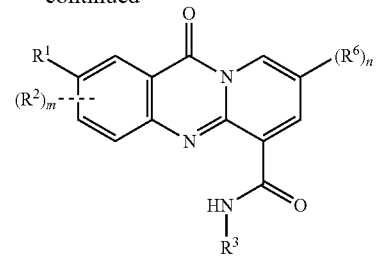

(Ib)

Reagents and Conditions:

Step d) $R^1$—$B(OH)_2$, Pd-Cat.; or amines

Step e) $R^6$—$B(OH)_2$, Pd-Cat.

In the above scheme, compounds of formula (I) are compounds according to the present invention wherein $R^1$, $R^2$, $R^3$ and $R^6$ are as hereinabove defined.

Pharmacological Activity

Functional Assays of Protein Kinases

The functional assays of protein Janus kinases were carried out in 384-well plates using a final volume of 30 μl. The reaction begins through the combination between the kinase enzyme and the peptic substrates (indicated in the table wherein the prefix 5-FAM indicates that the amino terminal group of the peptide is linked to 5-carboxyfluorescein and $CONH_2$ indicates that the carboxylic acid terminal group is amidated) in a concentration of 1.5 μM in presence of ATP and non-ATP controls. The reaction was reads in a "Caliper EzReader LabChip 3000" (Caliper, Hopkinton, Mass.) reader, based on electrophoretic mobility of the fluorescent substrate and the phosphorylated product.

The inhibition percentages were calculated by comparison between control reactions, for 100% of inhibition and reactions with only DMSO for 0% of inhibition. The reaction conditions were the following:

| Enzymes | Substrate | Buffer | ATP Concentration | Incubation (min) |
| --- | --- | --- | --- | --- |
| JAK1 (Product No.: 08-144, Carna Biosciences) | 5-FAM-KKSRGDYMTMQ IG-$CONH_2$ (5-FAM-SEQ ID NO: 1-$CONH_2$) | 100 mM Hepes pH = 7.2, 0.015% Brij-35, 4 mM DTT, 2% DMSO, 10 mM $MgCl_2$. | 100 μM | 150 |
| JAK2 (Product No.: 08-045, Carna Biosciences) | 5-FAM-EEPLYWSFPAKKK-$CONH_2$ (5-FAM-SEQ ID NO: 2-$CONH_2$) | 100 mM Hepes pH = 7.5, 4% DMSO, 0.003% Brij, 0.004% Tween 20, 100 mM $MgCl_2$. | 300 μM | 30 |
| JAK3 (Product No.: 08-046, Carna Biosciences) | 5-FAM-EEPLYWSFPAKKK-$CONH_2$ (5-FAM-SEQ ID NO: 2-$CONH_2$) | 20m Hepes pH7.4, 0.01% BSA X-100, 0.005% Tween 20, 2% DMSO, 10 mM $MgCl_2$. | 8 μM | 30 |
| TYK2 (Product No.: 08-147, Carna Biosciences) | 5-FAM-KKSRGDYMTMQ IG-$CONH_2$ (5-FAM-SEQ ID NO: 1-$CONH_2$) | 100 mM Hepes pH = 7.2, 0.015% Brij-35, 4 mM DTT, 2%DMSO, 10 mM $MgCl_2$. | 20 μM | 45 |

ARK5 Activity Inhibition Test

Activity test was carried out using the kit from Reaction Biology (CAT #: ARK5/NUAK1). The test uses enzyme Human ARK5/NUAK1 and the substrate is the peptide KKKVSRSGLYRSPSMPENLNRPR (SEQ ID NO: 1), 20 µM and ATP 10 µM. Other reagents are the following: Base Reaction buffer; 20 mM Hepes (pH 7.5), 10 mM $MgCl_2$, 1 mM EGTA, 0.02% Brij35, 0.02 mg/ml BSA, 0.1 mM $Na_3VO_4$, 2 mM DTT, 1% DMSO.

The reaction was carried out following the instructions of manufacturer. Briefly, kinase/substrate pairs were prepared in reaction buffer. Compounds were delivered into the reaction, followed 20 minutes later by addition of a mixture of ATP (Sigma, St. Louis Mo.) and $^{33}P$ ATP (Perkin Elmer, Waltham Mass.) to a final concentration of 10 µM. Reactions were carried out at room temperature for 120 min, followed by spotting of the reactions onto P81 ion exchange filter paper (Whatman Inc., Piscataway, N.J.). Unbound phosphate was removed by extensive washing of filters in 0.75% phosphoric acid. After subtraction of background derived from control reactions containing inactive enzyme, kinase activity data was expressed as the percent remaining kinase activity in test samples compared to vehicle (dimethyl sulfoxide) reactions. $IC_{50}$ values and curve fits were obtained using Prism (GraphPad Software).

Results

Table 1 shows how various compounds of the present invention score in a three-level classification according to their enzymatic activity ($IC_{50}$) values.

TABLE 1

| Ex. | Compound | ARK5 | JAK1 | JAK2 | JAK3 | TYK2 |
|---|---|---|---|---|---|---|
| 1 | N-cyclohexyl-2-cyclopropyl-11-oxo-11H-pyrido[2,1-b]quinazoline-6-carboxamide | A | C | C | A | A |
| 2 | N-cyclopentyl-2-cyclopropyl-11-oxo-11H-pyrido[2,1-b]quinazoline-6-carboxamide | A | C | C | A | A |
| 3 | 2-cyclopropyl-N-(1-methylpiperidin-4-yl)-11-oxo-11H-pyrido[2,1-b]quinazoline-6-carboxamide | — | C | C | B | C |
| 4 | 2-cyclopropyl-11-oxo-N-(tetrahydro-2H-pyran-4-yl)-11H-pyrido[2,1-b]quinazoline-6-carboxamide | — | C | C | B | A |
| 5 | 2-cyclopropyl-N-(3-methyltetrahydro-2H-pyran-4-yl)-11-oxo-11H-pyrido[2,1-b]quinazoline-6-carboxamide | — | C | C | A | A |
| 6 | 2-cyclopropyl-N-((1R,4R)-4-hydroxy-4-methylcyclohexyl)-11-oxo-11H-pyrido[2,1-b]quinazoline-6-carboxamide | — | C | C | A | A |
| 7 | 2-cyclopropyl-N-((1R,4R)-4-hydroxycyclohexyl)-11-oxo-11H-pyrido[2,1-b]quinazoline-6-carboxamide | — | C | C | A | B |
| 8 | 2-cyclopropyl-N-(2-hydroxycyclohexyl)-11-oxo-11H-pyrido[2,1-b]quinazoline-6-carboxamide | — | C | C | B | A |
| 9 | 2-cyclopropyl-N-((1R,2R)-2-hydroxycyclohexyl)-11-oxo-11H-pyrido[2,1-b]quinazoline-6-carboxamide | — | C | C | B | C |
| 10 | 2-cyclopropyl-N-((1S,2R)-2-hydroxycyclohexyl)-11-oxo-11H-pyrido[2,1-b]quinazoline-6-carboxamide | — | C | C | A | A |
| 11 | 2-cyclopropyl-N-((1R,2S)-2-hydroxycyclohexyl)-11-oxo-11H-pyrido[2,1-b]quinazoline-6-carboxamide | — | C | C | A | B |
| 12 | 2-cyclopropyl-N-((1S,2S)-2-hydroxycyclohexyl)-11-oxo-11H-pyrido[2,1-b]quinazoline-6-carboxamide | — | C | C | B | B |
| 14 | 2-cyclopropyl-11-oxo-N-(tetrahydrofuran-3-yl)-11H-pyrido[2,1-b]quinazoline-6-carboxamide | — | C | C | B | A |
| 15 | 2-cyclopropyl-N-(4,4-difluorocyclohexyl)-11-oxo-11H-pyrido[2,1-b]quinazoline-6-carboxamide | — | C | C | A | B |
| 18 | N-cyclopentyl-2-hydroxy-11-oxo-11H-pyrido[2,1-b]quinazoline-6-carboxamide | — | C | C | B | A |
| 20 | N-cyclohexyl-2-methoxy-11-oxo-11H-pyrido[2,1-b]quinazoline-6-carboxamide | A | — | — | A | A |
| 24 | N-cyclohexyl-2-fluoro-11-oxo-11H-pyrido[2,1-b]quinazoline-6-carboxamide | — | C | C | B | B |
| 25 | 2-bromo-N-cyclopentyl-11-oxo-11H-pyrido[2,1-b]quinazoline-6-carboxamide | — | C | C | A | A |
| 26 | 2-bromo-N-cyclohexyl-11-oxo-11H-pyrido[2,1-b]quinazoline-6-carboxamide | — | C | C | B | B |
| 27 | 2-bromo-N-((1S,2R)-2-hydroxycyclohexyl)-11-oxo-11H-pyrido[2,1-b]quinazoline-6-carboxamide | — | C | C | B | B |
| 28 | N-cyclohexyl-11-oxo-2-phenyl-11H-pyrido[2,1-b]quinazoline-6-carboxamide | — | C | C | B | B |
| 29 | N-cyclohexyl-2-(4-fluorophenyl)-11-oxo-11H-pyrido[2,1-b]quinazoline-6-carboxamide | A | C | C | B | C |
| 31 | N-cyclohexyl-2-(4-methylpiperazin-1-yl)-11-oxo-11H-pyrido[2,1-b]quinazoline-6-carboxa | A | C | C | A | A |

TABLE 1-continued

| Ex. | Compound | ARK5 | JAK1 | JAK2 | JAK3 | TYK2 |
|---|---|---|---|---|---|---|
| 32 | N-cyclopentyl-11-oxo-2-(pyridin-4-yl)-11H-pyrido[2,1-b]quinazoline-6-carboxamide | — | C | C | B | A |
| 33 | N-cyclohexyl-11-oxo-2-(pyridin-4-yl)-11H-pyrido[2,1-b]quinazoline-6-carboxamide | A | C | C | A | A |
| 34 | N-((1S,2R)-2-hydroxycyclohexyl)-11-oxo-2-(pyridin-4-yl)-11H-pyrido[2,1-b]quinazoline-6-carboxamide | — | C | C | B | B |
| 35 | N-cyclopentyl-2-(4-methylpiperazin-1-yl)-11-oxo-11H-pyrido[2,1-b]quinazoline-6-carboxamide | — | C | C | A | B |
| 36 | N-cyclohexyl-2-(4-methylpiperazin-1-yl)-11-oxo-11H-pyrido[2,1-b]quinazoline-6-carboxamide | A | C | C | A | A |
| 37 | N-((1S,2R)-2-hydroxycyclohexyl)-2-(4-methylpiperazin-1-yl)-11-oxo-11H-pyrido[2,1-b]quinazoline-6-carboxamide | — | — | — | B | A |
| 38 | N-cyclohexyl-2-morpholino-11-oxo-11H-pyrido[2,1-b]quinazoline-6-carboxamide | A | C | C | A | A |

Ranges

A compound is assigned score A when its $IC_{50}$ is lower than 100 nM

A compound is assigned score B when its $IC_{50}$ ranges between 100 nM and less than 1 μM.

A compound is assigned score C when its $IC_{50}$ is greater than 1 μM.

As can be seen from the results described in Table 1, the compounds of the present invention are potent inhibitors of at least one kinases selected from ARK5, JAK3 and TYK2, showing good selectivity against the enzymes JAK1 and JAK2.

The derivatives of the invention are useful in the treatment or prevention of diseases known to be susceptible to improvement by treatment with an inhibitor of at least one protein kinase selected from ARK5, JAK3 and TYK2. Such diseases are autoimmune diseases including psoriasis, atopic dermatitis, rheumatoid arthritis, multiple sclerosis, alopecia areata, lupus, inflammatory bowel diseases including ulcerative colitis and Crohn's disease, cancer such as blood cancer, gastric cancer, colon cancer, colorectal cancer, liver cancer, lung cancer, pancreatic cancer, breast cancer, and other solid tumours, and others diseases such as asthma, chronic obstructive pulmonary disease (COPD), transplant rejection, haematological disease, uveitis, dry eye and allergic conjunctivitis, among others.

Accordingly, the derivatives of the invention and pharmaceutically acceptable salts thereof, and pharmaceutical compositions comprising such compounds and/or salts thereof, may be used in a method of treatment of disorders of the human body which comprises administering to a subject requiring such treatment an effective amount of the 11-oxo-11H-pyrido[2,1-b]quinazoline-6-carboxamide derivatives of the invention or a pharmaceutically acceptable salt thereof.

The present invention also provides pharmaceutical compositions which comprise, as an active ingredient, at least a 11-oxo-11H-pyrido[2,1-b]quinazoline-6-carboxamide derivatives of formula (I) or a pharmaceutically acceptable salt thereof in association with, others therapeutics agents a pharmaceutically acceptable excipient such as a carrier or diluent. The active ingredient may comprise 0.001% to 99% by weight, preferably 0.01% to 90% by weight of the composition depending upon the nature of the formulation and whether further dilution is to be made prior to application.

Preferably, compounds of formula (I), pharmaceutically acceptable salts and compositions thereof are made up in a form suitable for oral, topical, nasal, rectal, percutaneous or injectable administration.

The pharmaceutically acceptable excipients, which are admixed with the active compound or salts of such compound, to form the compositions of this invention, are well known per se and the actual excipients used depend inter alia on the intended method of administering the compositions.

Compounds of formula (I), pharmaceutically salts thereof and compositions of this invention are preferably adapted for injectable and per os administration. In this case, the compositions for oral administration may take the form of tablets, retard tablets, sublingual tablets, capsules, inhalation aerosols, inhalation solutions, dry powder inhalation, or liquid preparations, such as mixtures, elixirs, syrups or suspensions, all containing the compound of the invention; such preparations may be made by methods well-known in the art.

The diluents, which may be used in the preparation of the compositions, include those liquid and solid diluents, which are compatible with the active ingredient, together with colouring or flavouring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in pyrogen free aqueous media or other appropriate parenteral injection fluid.

Effective doses are normally in the range of 2-2000 mg of active ingredient per day. Daily dosage may be administered in one or more treatments, preferably from 1 to 4 treatments, per day.

The present invention will be further illustrated by the following examples. The following are given by way of illustration and do not limit the scope of the invention in any way. The synthesis of the compounds of the invention is illustrated by the following examples including the preparation of the intermediates, which do not limit the scope of the invention in any way.

ABBREVIATIONS

In the present application are used the following abbreviations, with the corresponding definitions:
HCl: Hydrochloric acid
HATU: N-[(Dimethylamino)-1H-1,2,3-triazolo-[4,5-b]pyridin-1-ylmethylene]-N-methylmethanaminium hexafluorophosphate N-oxide
EDC: N-(3-Dimethylaminopropyl)-N'-ethylcarbodiimide
HOBt: 1-Hydroxybenzotriazole
T3 P: 2,4,6-tripropyl-1,3,5,2,4,6-trioxatriphosphinane 2,4,6-trioxide
EDIA: diisopropylethylamine
DIPEA: N,N-Diisopropylethylamine
THF: tetrahydrofurane
DCM: dichloromethane
DMF: dimethylformamide
CDCl$_3$: deuterated chloroform
DMSO: dimethylsulfoxide
Pd-Cat: palladium catalyst
Pd(AcO)$_2$: palladium (II) acetate
R$^1$—B(OH)$_2$: boronic acid derivative of R$^1$
MeOH: methanol
AcOH: acetic acid

EXAMPLES

General. Reagents, solvents and starting products were acquired from commercial sources. The term "concentration" refers to the vacuum evaporation using a Büchi rotavapor. When indicated, the reaction products were purified by "flash" chromatography on silica gel (40-63 μm) with the indicated solvent system. The spectroscopic data were measured in a Varian Mercury 400 spectrometer. The melting points were measured in a Büchi 535 instrument. The HPLC-MS were performed on a Gilson instrument equipped with a Gilson 321 piston pump, a Gilson 864 vacuum degasser, a Gilson 189 injection module, a 1/1000 Gilson splitter, a Gilson 307 pump, a Gilson 170 detector, and a Thermoquest Fennigan aQa detector.

Intermediate 1: methyl 2-amino-5-cyclopropylbenzoate

A mixture of methyl 2-amino-5-bromobenzoate (800 mg, 4.18 mmol), cyclopropylboronic acid (776 mg, 10.87 mmol), K$_3$PO$_4$ (2.44 g, 14.0 mmol), Pd(AcO)$_2$ (64 mg, 0.33 mmol) and P(Cy)$_3$ (176 mg, 0.79 mmol) was suspended in toluene (15 mL) and water (0.8 mL) under nitrogen atmosphere and heated for 2 hours at 100° C. The reaction mixture was filtered through celite and the organic phase was separated, dried and the solvent was removed under reduced pressure, affording 0.65 g (yield 81%).
$^1$H-RMN (400 MHz, CDCl$_3$): δ=7.60 (m, 1H), 7.05 (dd, 1H), 6.65 (d, 1H), 1.81 (m, 3H), 0.86 (m, 2H), 0.59 (m, 2H).
HPLC-MS: Rt: 4.656 min, m/z: 192.0 (MH$^+$).

Intermediate 2: methyl 4-amino-[1,1'-biphenyl]-3-carboxylate

A mixture of methyl 2-amino-5-bromobenzoate (1000 mg, 4.35 mmol), phenylboronic acid (1060 mg, 8.70 mmol), K$_3$PO$_4$ (2330 mg, 10.88 mmol), Pd(AcO)$_2$ (80 mg, 0.35 mmol) and P(Cy)$_3$ (220 mg, 0.80 mmol) was suspended in toluene (20 mL) and water (1.0 mL) under nitrogen atmosphere and heated for 2 hours at 100° C. The reaction mixture was filtered through celite and the organic phase was separated, dried and the solvent was removed under reduced pressure, affording 931 mg (yield 95%).
$^1$H-RMN (400 MHz, CDCl$_3$): δ=8.13 (d, 1H), 7.55 (m, 3H), 7.40 (m, 2H), 7.28 (m, 1H), 6.75 (d, 1H), 5.79 (s, 2H), 3.90 (s, 3H).
HPLC-MS: Rt: 5.051 min, m/z: 228.1 (MH$^+$).

Intermediate 3: methyl 4-amino-4'-fluoro-[1,1'-biphenyl]-3-carboxylate $^1$H-RMN (400 MHz, CDCl$_3$): δ=8.06 (d, 1H), 7.48 (m, 3H), 7.09 (m, 2H), 6.74 (d, 1H), 5.79 (s, 2H), 3.90 (s, 3H).
HPLC-MS: Rt: 5.156 min, m/z: 246.0 (MH$^+$)

Intermediate 4: methyl 2-amino-5-(thiophen-2-yl)benzoate

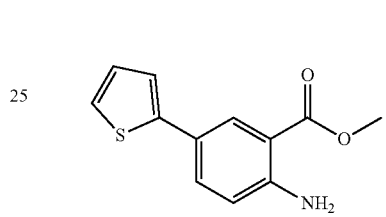

$^1$H-RMN (400 MHz, CDCl$_3$): δ=8.11 (d, 1H), 7.53 (dd, 1H), 7.18 (m, 2H), 7.04 (dd, 1H), 6.69 (d, 1H), 5.80 (s, 2H), 3.91 (s, 3H).
HPLC-MS: 4.752 min, m/z: 252.9 (MH$^+$).

Intermediate 5: 2-cyclopropyl-11-oxo-11H-pyrido[2,1-b]quinazoline-6-carboxylic acid A mixture of methyl 2-amino-5-cyclopropylbenzoate (631 mg, 3.3 mmol), 2-chloronicotinic acid (521 mg, 3.3 mmol) and hydrochloric acid (0.54 mL, 17.8 mmol) in ethanol (8 mL) was stirred at 80° C. for 48 hours. After cooling, the suspension was filtered, washed with cool ethanol and n-pentane and dried. 0.5 g of product was obtained (54% yield).
$^1$H-RMN (400 MHz, DMSO-d$_6$): δ=9.02 (dd, 1H), 8.60 (dd, 1H), 8.00 (m, 1H), 7.78 (d, 1H), 7.69 (dd, 2H), 7.25 (t, 1H), 2.19 (m, 2H), 1.08 (m, 2H), 0.82 (m, 2H).
HPLC-MS: Rt: 2.36 min, m/z: 281.1 (MH$^+$).
The following intermediates 6-17 were synthetized using the corresponding commercial derivatives of methyl 2-aminobenzoate and 2-chloronicotinic acid.

Intermediate 6: 2-fluoro-11-oxo-11H-pyrido[2,1-b]quinazoline-6-carboxylic acid $^1$H-RMN (400 MHz, DMSO-d$_6$): δ=9.04 (d, 1H), 8.63 (d, 1H), 8.04 (m, 2H), 7.93 (m, 1H), 7.30 (t, 1H).
HPLC-MS: Rt: 1.35 min, m/z: 259.0 (MH$^+$).

Intermediate 7: 2-bromo-11-oxo-11H-pyrido[2,1-b]quinazoline-6-carboxylic acid $^1$H-RMN (400 MHz, DMSO-d$_6$): δ=16.29 (s, 1H), 9.06 (dd, 1H), 8.65 (dd, 1H), 8.42 (m, 1H), 8.12 (dd, 1H), 7.87 (t, 1H), 7.30 (t, 1H).
HPLC-MS: Rt: 1.74 min, m/z: 321.0 (MH$^+$).

Intermediate 8: 2-hydroxy-11-oxo-11H-pyrido[2,1-b]quinazoline-6-carboxylic acid ¹H-RMN (400 MHz, DMSO-d₆): δ=9.01 (dd, 1H), 8.58 (dd, 1H), 7.82 (t, 1H), 7.61 (d, 1H), 7.52 (dd, 1H), 7.23 (t, 1H), 4.43 (s, 1H).
HPLC-MS: Rt: 5.27 min, m/z: 254.1 (MH⁺).

Intermediate 9: 2-methoxy-11-oxo-11H-pyrido[2,1-b]quinazoline-6-carboxylic acid ¹H-RMN (400 MHz, DMSO-d₆): δ=9.03 (dd, 1H), 8.58 (dd, 1H), 7.90 (d, 1H), 7.67 (dd, 1H), 7.53 (m, 1H), 7.25 (t, 1H), 3.94 (s, 3H).
HPLC-MS: Rt: 1.731 min, m/z: 271.0 (MH⁺).

Intermediate 10: 11-oxo-2-(trifluoromethoxy)-11H-pyrido[2,1-b]quinazoline-6-carboxylic acid ¹H-RMN (400 MHz, DMSO-d₆): δ=9.05 (dd, 1H), 8.67 (dd, 1H), 8.19 (d, 1H), 8.08 (m, 1H), 7.97 (m, 1H), 7.33 (t, 1H).
HPLC-MS: Rt: 2.854 min, m/z: 325.0 (MH⁺).

Intermediate 11: 2-methyl-11-oxo-11H-pyrido[2,1-b]quinazoline-6-carboxylic acid ¹H-RMN (400 MHz, DMSO-d₆): δ=9.03 (dd, 1H), 8.63 (dd, 1H), 8.03 (m, 2H), 7.92 (m, 1H), 7.28 (t, 1H), 2.50 (s, 3H).
HPLC-MS: Rt: 1.27 min, m/z: 259.0 (MH⁺).

Intermediate 12: 11-oxo-2-phenyl-11H-pyrido[2,1-b]quinazoline-6-carboxylic acid ¹H-RMN (400 MHz, DMSO-d₆): δ=9.07 (dd, 1H), 8.64 (dd, 1H), 8.51 (d, 1H), 8.32 (dd, 1H), 7.97 (d, 1H), 7.82 (m, 2H), 7.53 (t, 2H), 7.44 (m, 1H), 7.29 (t, 1H).
HPLC-MS: Rt: 3.068 min, m/z: 317.0 (MH⁺).

Intermediate 13: 2-(4-fluorophenyl)-11-oxo-11H-pyrido[2,1-b]quinazoline-6-carboxylic acid ¹H-RMN (400 MHz, DMSO-d₆): δ=9.09 (dd, 1H), 8.65 (dd, 1H), 8.54 (d, 1H), 8.34 (dd, 1H), 8.01 (d, 1H), 7.91 (m, 2H), 7.37 (m, 2H), 7.30 (t, 1H).
HPLC-MS: Rt: 3.157 min, m/z: 335.0 (MH⁺).

Intermediate 14: 11-oxo-2-(thiophen-2-yl)-11H-pyrido[2,1-b]quinazoline-6-carboxylic acid ¹H-RMN (400 MHz, DMSO-d₆): δ=13.78 (s, 1H), 9.07 (dd, 1H), 8.64 (dd, 1H), 8.42 (d, 1H), 8.34 (dd, 1H), 7.97 (d, 1H), 7.77 (d, 1H), 7.67 (d, 1H), 7.30 (t, 1H), 7.22 (dd, 1H).
HPLC-MS: Rt: 3.083 min, m/z: 323.0 (MH⁺).

Intermediate 15: 2-cyclopropyl-8-methyl-11-oxo-11H-pyrido[2,1-b]quinazoline-6-carboxylic acid ¹H-RMN (400 MHz, DMSO-d₆): δ=8.85 (dd, 1H), 8.50 (d, 1H), 7.99 (d, 1H), 7.77 (d, 1H), 7.67 (dd, 1H), 2.42 (s, 3H), 2.18 (m, 1H), 1.08 (m, 2H), 0.82 (m, 2H).
HPLC-MS: Rt: 2.917 min, m/z: 295.0 (MH⁺).

Intermediate 16: 11-oxo-2-(trifluoromethyl)-11H-pyrido[2,1-b]quinazoline-6-carboxylic acid ¹H-RMN (400 MHz, DMSO-d₆): δ=9.12 (dd, 1H), 8.72 (dd, 1H), 8.26 (dd, 1H), 8.11 (d, 1H), 7.91 (d, 1H), 7.37 (t, 1H).
HPLC-MS: Rt: 2.845 min, m/z: 309.0 (MH⁺).

Intermediate 17: 2-fluoro-8-methyl-11-oxo-11H-pyrido[2,1-b]quinazoline-6-carboxylic acid ¹H-RMN (400 MHz, DMSO-d₆): δ=8.88 (s, 1H), 8.54 (d, 1H), 8.03 (m, 2H), 7.91 (m, 1H), 2.43 (s, 3H)
HPLC-MS: Rt: 2.431 min, m/z: 272.8 (MH⁺).

EXAMPLES

Example 1: N-cyclohexyl-2-cyclopropyl-11-oxo-11H-pyrido[2,1-b]quinazoline-6-carboxamide A mixture of 2-cyclopropyl-11-oxo-11H-pyrido[2,1-b]quinazoline-6-carboxylic acid (220 mg, 0.78 mmol), EDC (166 mg, 0.86 mmol) and HOBt (117 mg, 0.86 mmol) in DMF (1 mL) was stirred 10 min at room temperature. Then cyclohexanilamine (0.108 mL, 0.94 mmol) was added and the mixture was stirred 18 hours at room temperature. The product was precipitated in cool water, filtered, dried and purified through flash column chromatography (hexanes: AcOEt 8:2). (76% yield).
¹H-RMN (400 MHz, DMSO-d₆): δ=11.11 (d, 1H), 8.98 (dd, 1H), 8.57 (dd, 1H), 8.01 (d, 1H), 7.76-7.61 (m, 2H), 7.17 (s, 1H), 3.97 (s, 1H), 2.19 (s, 1H), 1.91 (s, 2H), 1.75 (d, 2H), 1.49 (d, 6H), 1.08 (d, 2H), 0.82 (d, 2H).
HPLC-MS: Rt: 5.55 min, m/z: 362.1 (MH⁺).

Example 2: N-cyclopentyl-2-cyclopropyl-11-oxo-11H-pyrido[2,1-b]quinazoline-6-carboxamide ¹H-RMN (400 MHz, DMSO-d₆): δ=11.05 (d, 1H), 8.94 (dd, 1H), 8.53 (dd, 1H), 7.97 (m, 1H), 7.64 (m, 2H), 7.15 (t, 1H), 4.4 (m, 1H), 2.16 (m, 1H), 1.75 (m, 8H), 1.07 (m, 2H), 0.80 (m, 2H).
HPLC-MS: Rt: 5.25 min, m/z: 348.1 (MH⁺).

Example 3: 2-cyclopropyl-N-(1-methylpiperidin-4-yl)-11-oxo-11H-pyrido[2,1-b]quinazoline-6-carboxamide ¹H-RMN (400 MHz, DMSO-d₆): δ=11.05 (d, 1H), 8.97 (dq, 1H), 8.53 (dq, 1H), 7.99 (d, 1H), 7.67 (d, 2H), 7.16 (td, 1H), 3.99 (s, 1H), 2.91 (m, 2H), 2.50 (s, 3H), 2.18 (m, 1H), 2.06 (m, 2H), 1.76 (m, 2H), 1.07 (dt, 2H), 0.81 (dt, 2H).
HPLC-MS: Rt: 3.29 min, m/z: 377.1 (MH$^+$).

Example 4: 2-cyclopropyl-11-oxo-N-(tetrahydro-2H-pyran-4-yl)-11H-pyrido[2,1-b]quinazoline-6-carboxamide $^1$H-RMN (400 MHz, DMSO-d$_6$): δ=11.12 (d, 1H), 8.97 (dd, 1H), 8.55 (dd, 1H), 7.99 (d, 1H), 7.69 (m, 2H), 7.16 (t, 1H), 4.12 (m, 1H), 3.90 (dt, 2H), 3.54 (ddd, 2H), 2.18 (tt, 1H), 1.97 (dd, 2H), 1.67 (dtd, 2H), 1.08 (m, 2H), 0.81 (dt, 2H).
HPLC-MS: Rt: 3.73 min, m/z: 364.1 (MH$^+$).

Example 5: 2-cyclopropyl-N-(3-methyltetrahydro-2H-pyran-4-yl)-11-oxo-11H-pyrido[2,1-b]quinazoline-6-carboxamide $^1$H-RMN (400 MHz, DMSO-d$_6$): δ=11.25 (d, 1H), 8.97 (dd, 1H), 8.59 (dd, 1H), 8.00 (m, 1H), 7.69 (m, 2H), 7.16 (dt, 1H), 4.35 (m, 1H), 3.71 (m, 4H), 2.17 (m, 1H), 2.09 (m, 1H), 1.82 (m, 2H), 1.07 (m, 2H), 0.99 (d, 3H), 0.81 (m, 2H).
HPLC-MS: Rt: 4.991 min, m/z: 378.0 (MH$^+$).

Example 6: 2-cyclopropyl-N-((1R,4R)-4-hydroxy-4-methylcyclohexyl)-11-oxo-11H-pyrido[2,1-b]quinazoline-6-carboxamide $^1$H-RMN (400 MHz, DMSO-d$_6$): δ=11.10 (d, 1H), 8.96 (m, 1H), 8.57 (dd, 1H), 7.99 (d, 1H), 7.69 (dd, 1H), 7.59 (d, 1H), 7.16 (t, 1H), 4.29 (s, 1H), 4.07 (m, 1H), 2.17 (m, 1H), 1.97 (m, 2H), 1.60 (6H), 1.22 (s, 3H), 1.07 (m, 2H), 0.81 (m, 2H).
HPLC-MS: Rt: 4.627 min, m/z: 392.1 (MH+).

Example 7: 2-cyclopropyl-N-((1R,4R)-4-hydroxycyclohexyl)-11-oxo-11H-pyrido[2,1-b]quinazoline-6-carboxamide $^1$H-RMN (400 MHz, DMSO-d$_6$): δ=11.01 (d, 1H), 8.95 (dq, 1H), 8.54 (dq, 1H), 7.96 (d, 1H), 7.66 (d, 2H), 7.15 (td, 1H), 4.63 (d, 1H), 3.77 (m, 1H), 3.58 (m, 1H), 2.17 (m, 1H), 2.04 (m, 2H), 1.89 (dd, 2H), 1.42 (m, 4H), 1.07 (m, 2H), 0.80 m, 2H).
HPLC-MS: Rt: 3.42 min, m/z: 378.1 (MH$^+$).

Example 8: 2-cyclopropyl-N-(2-hydroxycyclohexyl)-11-oxo-11H-pyrido[2,1-b]quinazoline-6-carboxamide $^1$H-RMN (400 MHz, DMSO-d$_6$): δ=11.47 (d, 1H), 8.97 (dd, 1H), 8.60 (m, 1H), 8.00 (d, 1H), 7.71 (m 2H) 7.16 (t, 1H), 5.02 (d, 1H), 3.97 (m, 1H), 3.87 (m, 1H), 2.18 (m, 1H), 1.68 (m, 5H), 1.38 (m, 2H), 1.24 (m, 1H), 1.07 (m, 2H), 0.82 (m, 2H).
HPLC-MS: Rt: 4.874 min, m/z: 378.0 (MH$^+$).

Example 9: 2-cyclopropyl-N-((1R,2R)-2-hydroxycyclohexyl)-11-oxo-11H-pyrido[2,1-b]quinazoline-6-carboxamide $^1$H-RMN (400 MHz, DMSO-d$_6$): δ=11.11 (d, 1H), 8.97 (dd, 1H), 8.54 (m, 1H), 7.99 (s, 1H), 7.69 (m 2H) 7.17 (dt, 1H), 4.92 (d, 1H), 3.73 (m, 1H), 3.55 (m, 1H), 2.15 (m, 1H), 1.93 (m, 1H), 1.68 (m, 2H), 1.315 (m, 5H), 1.07 (m, 2H), 0.81 (m, 2H).
HPLC-MS: Rt: 4.891 min, m/z: 378.0 (MH$^+$).

Example 10: 2-cyclopropyl-N-((1S,2R)-2-hydroxycyclohexyl)-11-oxo-11H-pyrido[2,1-b]quinazoline-6-carboxamide $^1$H-RMN (400 MHz, DMSO-d$_6$): δ=11.47 (d, 1H), 8.97 (dd, 1H), 8.60 (m, 1H), 8.00 (d, 1H), 7.71 (m 2H) 7.16 (t, 1H), 5.02 (d, 1H), 3.97 (m, 1H), 3.87 (m, 1H), 2.18 (m, 1H), 1.68 (m, 5H), 1.38 (m, 2H), 1.24 (m, 1H), 1.07 (m, 2H), 0.82 (m, 2H).
HPLC-MS: Rt: 4.819 min, m/z: 378.0 (MH$^+$).

Example 11: 2-cyclopropyl-N-((1R,2S)-2-hydroxycyclohexyl)-11-oxo-11H-pyrido[2,1-b]quinazoline-6-carboxamide $^1$H-RMN (400 MHz, DMSO-d$_6$): δ=11.47 (d, 1H), 8.97 (dd, 1H), 8.60 (m, 1H), 8.00 (d, 1H), 7.71 (m 2H) 7.16 (t, 1H), 5.02 (d, 1H), 3.97 (m, 1H), 3.87 (m, 1H), 2.18 (m, 1H), 1.68 (m, 5H), 1.38 (m, 2H), 1.24 (m, 1H), 1.07 (m, 2H), 0.82 (m, 2H).
HPLC-MS: Rt: 4.818 min, m/z: 378.0 (MH$^+$).

Example 12: 2-cyclopropyl-N-((1S,2S)-2-hydroxycyclohexyl)-11-oxo-11H-pyrido[2,1-b]quinazoline-6-carboxamide $^1$H-RMN (400 MHz, DMSO-d$_6$): δ=11.11 (d, 1H), 8.97 (dd, 1H), 8.54 (m, 1H), 7.99 (s, 1H), 7.69 (m 2H) 7.17 (dt, 1H), 4.92 (d, 1H), 3.73 (m, 1H), 3.55 (m, 1H), 2.15 (m, 1H), 1.93 (m, 1H), 1.68 (m, 2H), 1.315 (m, 5H), 1.07 (m, 2H), 0.81 (m, 2H).
HPLC-MS: Rt: 4.855 min, m/z: 378.0 (MH$^+$).

Example 13: N-((1R,4R)-4-aminocyclohexyl)-2-cyclopropyl-11-oxo-11H-pyrido[2,1-b]quinazoline-6-carboxamide $^1$H-RMN (400 MHz, DMSO-d$_6$): δ=11.02 (d, 1H), 8.97 (dd, 1H), 8.54 (m, 1H), 7.99 (d, 1H), 7.71 (m, 2H), 7.31 (m, 1H), 7.15 (m, 1H), 3.81 (m, 1H), 3.65 (m, 1H), 2.13 (m, 5H), 1.53 (m, 4H), 1.07 (m, 2H), 0.85 (m, 2H).
HPLC-MS: Rt: 3.01 min, m/z: 377.2 (MH$^+$).

Example 14: 2-cyclopropyl-11-oxo-N-(tetrahydrofuran-3-yl)-11H-pyrido[2,1-b]quinazoline-6-carboxamide $^1$H-RMN (400 MHz, DMSO-d$_6$): δ=11.27 (d, 1H), 8.96 (dd, 1H), 8.54 (dd, 1H), 7.98 (d, 1H), 7.66 (dt, 2H), 7.16 (t, 1H), 4.57 (m, 1H), 3.97 (dd, 1H), 3.87 (m, 2H), 3.74 (dd, 1H), 2.31 (ddd, 1H), 2.18 (m, 1H), 1.99 (ddd, 1H), 1.08 (m, 2H), 0.82 (m, 2H).
HPLC-MS: Rt: 4.633 min, m/z: 350.0 (MH$^+$).

Example 15: 2-cyclopropyl-N-(4,4-difluorocyclohexyl)-11-oxo-11H-pyrido[2,1-b]quinazoline-6-carboxamide $^1$H-RMN (400 MHz, CDCl$_3$): δ=11.48 (d, 1H), 9.04 (dd, 1H), 8.76 (dd, 1H), 8.10 (d, 1H), 7.62 (m, 2H), 7.01 (t, 1H), 4.25 (m, 1H), 2.12 (m, 7H), 1.87 (m, 2H), 1.11 (m, 2H), 0.85 (m, 2H).
HPLC-MS: Rt: 5.621 min, m/z: 398.1 (MH$^+$)

Example 16: N-cyclohexyl-2-cyclopropyl-8-methyl-11-oxo-11H-pyrido[2,1-b]quinazoline-6-carboxamide $^1$H-RMN (400 MHz, CDCl$_3$): δ=11.37 (d, 1H), 8.82 (s, 1H), 8.65 (d, 1H), 8.09 (s, 1H), 7.60 (m, 2H), 4.13 (m, 1H), 2.41 (s, 3H), 2.08 (m, 3H), 1.79 (m, 2H), 1.65 (m, 1H), 1.51 (m, 5H), 1.09 (m, 2H), 0.84 (m, 2H).
HPLC-MS: Rt: 6.363 min, m/z: 375.47 (MH$^+$).

Example 17: N-(4,4-difluorocyclohexyl)-2-fluoro-8-methyl-11-oxo-11H-pyrido[2,1-b]quinazoline-6-carboxamide

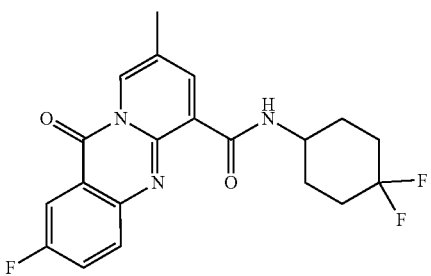 [SMILES: Cc1cc(C(=O)NC2CCC(F)(F)CC2)c2nc3ccc(F)cc3c(=O)n2c1]

$^1$H-RMN (400 MHz, CDCl$_3$): δ=11.33 (d, 1H), 8.84 (s, 1H), 8.69 (d, 1H), 8.07 (dd, 1H), 7.65 (m, 2H), 4.25 (m, 1H), 2.44 (s, 3H), 2.19 (m, 4H), 2.04 (m, 2H), 1.86 (m, 2H).
HPLC-MS: Rt: 5.373 min, m/z: 389.9 (MH$^+$).

Example 18: N-cyclopentyl-2-hydroxy-11-oxo-11H-pyrido[2,1-b]quinazoline-6-carboxamide $^1$H-RMN (400 MHz, DMSO-d$_6$): δ=11.07 (d, 1H), 10.28 (s, 1H), 8.90 (dd, 1H), 8.47 (dd, 1H), 7.63 (d, 1H), 7.56 (d, 1H), 7.49 (dd, 1H), 7.11 (t, 1H), 4.32 (dt, 1H), 1.97 (m, 2H), 1.79 (m, 2H), 1.67 (m, 4H).
HPLC-MS: Rt: 4.223 min, m/z: 324.0 (MH$^+$).

Example 19: N-cyclohexyl-2-hydroxy-11-oxo-11H-pyrido[2,1-b]quinazoline-6-carboxamide

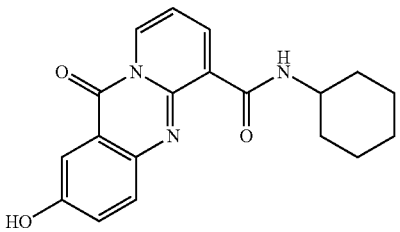 [SMILES: O=C(NC1CCCCC1)c1cccn2c(=O)c3cc(O)ccc3nc12]

$^1$H-RMN (400 MHz, CDCl$_3$): δ=11.10 (d, 1H), 10.29 (s, 1H), 8.92 (dd, 1H), 8.49 (dd, 1H), 7.68 (d, 1H), 7.58 (d, 1H), 7.51 (dd, 1H), 7.12 (t, 1H), 3.93 (m, 1H), 1.91 (m, 2H), 1.75 (m, 2H), 1.50 (m, 6H).
HPLC-MS: Rt: 4.518 min, m/z: 337.9 (MH$^+$).

Example 20: N-cyclohexyl-2-methoxy-11-oxo-11H-pyrido[2,1-b]quinazoline-6-carboxamide $^1$H-RMN (400 MHz, CDCl$_3$): δ=11.28 (d, 1H), 9.04 (dd, 1H), 8.77 (d, 1H), 7.75 (d, 1H), 7.68 (d, 1H), 7.52 (dd, 1H), 7.02 (t, 1H), 4.13 (m, 1H), 3.98 (s, 3H), 2.06 (m, 2H), 1.81 (m, 2H), 1.54 (m, 6H).
HPLC-MS: Rt: 5.376 min, m/z: 352.1 (MH$^+$).

Example 21: N-cyclohexyl-11-oxo-2-(trifluoromethoxy)-11H-pyrido[2,1-b]quinazoline-6-carboxamide $^1$H-RMN (400 MHz, CDCl$_3$): δ=11.09 (d, 1H), 9.04 (dd, 1H), 8.86 (dd, 1H), 8.27 (s, 1H), 7.74 (m, 2H), 7.09 (t, 1H), 4.13 (m, 1H), 2.06 (m, 2H), 1.81 (m, 2H), 1.65 (m, 1H), 1.48 (m, 5H).
HPLC-MS: Rt: 5.998 min, m/z: 406.1 (MH$^+$).

Example 22: N-cyclohexyl-2-methyl-11-oxo-11H-pyrido[2,1-b]quinazoline-6-carboxamide $^1$H-RMN (400 MHz, DMSO-d$_6$): δ=11.10 (d, 1H), 8.98 (dd, 1H), 8.56 (dd, 1H), 8.01 (d, 1H), 7.76-7.61 (m, 2H), 7.17 (s, 1H), 3.97 (s, 1H), 2.41 (s, 3H), 1.91 (s, 2H), 1.75 (d, 2H), 1.49 (d, 6H).

Example 23: N-cyclohexyl-11-oxo-2-(trifluoromethyl)-11H-pyrido[2,1-b]quinazoline-6-carboxamide $^1$H-RMN (400 MHz, CDCl$_3$): δ=11.06 (d, 1H), 9.08 (dd, 1H), 8.92 (dd, 1H), 8.75 (s, 1H), 8.05 (dd, 1H), 7.80 (d, 1H), 7.13 (t, 1H), 4.14 (m, 1H), 2.07 (m, 2H), 1.81 (m, 2H), 1.57 (m, 6H).
HPLC-MS: Rt 5.917 min, m/z: 389.8 (MH$^+$).

Example 24: N-cyclohexyl-2-fluoro-11-oxo-11H-pyrido[2,1-b]quinazoline-6-carboxamide $^1$H-RMN (400 MHz, DMSO-d$_6$): δ=10.93 (d, 1H), 8.95 (dd, 1H), 8.59 (dd, 1H), 7.98 (dd, 1H), 7.85 (m, 2H), 7.21 (t, 1H), 3.94 (m, 1H), 1.93 (m, 2H), 1.74 (m, 2H), 1.48 (m, 6H).
HPLC-MS: Rt: 5.03 min, m/z: 340.1 (MH$^+$).

Example 25: 2-bromo-N-cyclopentyl-11-oxo-11H-pyrido[2,1-b]quinazoline-6-carboxamide $^1$H-RMN (400 MHz, DMSO-d$_6$): δ=10.88 (d, 1H), 8.98 (dd, 1H), 8.61 (dd, 1H), 8.38 (d, 1H), 8.09 (dd, 1H), 7.67 (d, 1H), 7.22 (t, 1H), 4.32 (dd, 1H), 2.00 (m, 2H), 1.78 (m, 2H), 1.68 (m, 4H).
HPLC-MS: Rt: 5.626 min, m/z: 385.9 (MH$^+$).

Example 26: 2-bromo-N-cyclohexyl-11-oxo-11H-pyrido[2,1-b]quinazoline-6-carboxamide $^1$H-RMN (400 MHz, DMSO-d$_6$): δ=11.08 (d, 1H), 9.03 (dd, 1H), 8.85 (dd, 1H), 8.58 (d, 1H), 7.93 (dd, 1H), 7.59 (d, 1H), 7.07 (t, 1H), 4.12 (m, 1H), 2.06 (m, 2H), 1.81 (m, 2H), 1.53 (m, 6H).
HPLC-MS: Rt: 5.877 min, m/z: 399.9 (MH$^+$).

Example 27: 2-bromo-N-((1S,2R)-2-hydroxycyclohexyl)-11-oxo-11H-pyrido[2,1-b]quinazoline-6-carboxamide $^1$H-RMN (400 MHz, CDCl$_3$): δ=11.35 (m, 1H), 9.04 (dd, 1H), 8.92 (d, 1H), 8.57 (d, 1H), 7.93 (dd, 1H), 7.65 (d, 1H), 7.11 (t, 1H), 4.32 (m, 1H), 4.10 (m, 1H), 2.02 (s, 1H), 1.83 (m, 6H), 1.56 (m, 2H).
HPLC-MS: Rt: 4.757 min, m/z: 417.0 (MH$^+$).

Example 28: N-cyclohexyl-11-oxo-2-phenyl-11H-pyrido[2,1-b]quinazoline-6-carboxamide $^1$H-RMN (400 MHz, CDCl$_3$): δ=11.31 (d, 1H), 9.07 (dd, 1H), 8.83 (dd, 1H), 8.68 (m, 1H), 8.16 (dd, 1H), 7.80 (d, 1H), 7.75 (dd, 2H), 7.52 (m, 2H), 7.42 (m, 1H), 7.05 (t, 1H), 4.15 (m, 1H), 2.08 (m, 1H), 1.83 (m, 1H), 1.47 (m, 6H).
HPLC-MS: Rt: 6.304 min, m/z: 398.1 (MH$^+$).

Example 29: N-cyclohexyl-2-(4-fluorophenyl)-11-oxo-11H-pyrido[2,1-b]quinazoline-6-carboxamide $^1$H-RMN (400 MHz, CDCl3): δ=11.29 (d, 1H), 9.07 (dd, 1H), 8.83 (dd, 1H), 8.61 (d, 1H), 8.10 (dd, 1H), 7.79 (d, 1H), 7.70 (m, 2H), 7.20 (m, 2H), 7.05 (t, 1H), 4.15 (m, 1H), 2.08 (m, 2H), 1.83 (m, 2H), 1.65 (m, 1H), 1.51 (m, 5H).
HPLC-MS: Rt: 6.208 min, m/z: 416.1 (MH$^+$).

Example 30: N-cyclohexyl-11-oxo-2-(thiophen-2-yl)-11H-pyrido[2,1-b]quinazoline-6-carboxamide

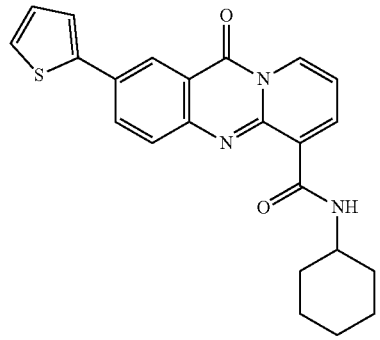 [SMILES: O=C(NC1CCCCC1)c1cccn2c(=O)c3cc(-c4cccs4)ccc3nc12]

HPLC-MS: Rt: 5.803 min, m/z: 404.1 (MH$^+$).

Example 31: 2-cyano-N-cyclohexyl-11-oxo-11H-pyrido[2,1-b]quinazoline-6-carboxamide A mixture of 2-bromo-N-cyclohexyl-11-oxo-11H-pyrido[2,1-b]quinazoline-6-carboxamide (70 mg, 0.175 mmol) and copper cyanide (24 mg, 0.263 mmol), in NMP (0.8 mL) was stirred under nitrogen atmosphere at 150° C. for 48 hours. The product was precipitated in sat. aq. NaHCO$_3$, filtered and the resulting solid was solved in AcOEt (10 mL), washed with sat. aq. NH$_4$OH/NH$_4$Cl (3×), dried over MgSO$_4$, filtered and the solvent was removed under reduced pressure. The product was purified through flash column chromatography (hexanes: AcOEt 4:1) to yield 18 mg of pure product as yellow solid (30% yield).
$^1$H-RMN (400 MHz, CDCl$_3$): δ=10.94 (d, 1H), 9.08 (dd, 1H), 8.97 (m, 1H), 8.79 (d, 1H), 8.01 (dd, 1H), 7.77 (d, 1H), 7.18 (t, 1H), 4.12 (m, 1H), 2.07 (m, 2H), 1.80 (m, 2H), 1.53 (m, 6H).
HPLC-MS: Rt: 5.080 min, m/z: 347.1 (MH+).

Example 32: N-cyclopentyl-11-oxo-2-(pyridin-4-yl)-11H-pyrido[2,1-b]quinazoline-6-carboxamide A mixture of 2-bromo-N-cyclopentyl-11-oxo-11H-pyrido[2,1-b]quinazoline-6-carboxamide (50 mg, 0.13 mmol), pyridin-4-yl boronic acid (22 mg, 0.18 mmol), Pd(PPh$_3$)$_4$ (3 mg, 0.0026 mmol) and 2N Cs$_2$CO$_3$ (0.13 mL, 0.26 mmol) in 1,4-dioxane (1 mL) was stirred under nitrogen atmosphere at 60° C. for 20 hours. The resulting suspension was filtered through silica gel, washed with 1N NaOH, sat. aq. NaHCO$_3$ and brine, dried over MgSO$_4$, filtered and concentrated. The product was isolated after washing with cool EtOH and pentane. 45% yield.

$^1$H-RMN (400 MHz, DMSO-d$_6$): δ=11.01 (d, 1H), 9.01 (dd, 1H), 8.69 (d, 2H), 8.62 (m, 2H), 8.39 (dd, 1H), 7.85 (dd, 2H), 7.80 (d, 1H), 7.23 (t, 1H), 4.34 (d, 1H), 2.01 (m, 2H), 1.72 (m, 6H).
HPLC-MS: Rt: 4.714 min, m/z: 385.0 (MH$^+$).

Example 33: N-cyclohexyl-11-oxo-2-(pyridin-4-yl)-11H-pyrido[2,1-b]quinazoline-6-carboxamide $^1$H-RMN (400 MHz, DMSO-d$_6$): δ=11.04 (d, 1H), 9.03 (dd, 1H), 8.67 (m, 4H), 8.41 (dd, 1H), 7.87 (m, 3H), 7.24 (t, 1H), 3.97 (m, 1H), 1.93 (m, 2H), 1.77 (m, 2H), 1.51 (m, 6H).
HPLC-MS: Rt: 5.025 min, m/z: 399.1 (MH$^+$).

Example 34: N-((1S,2R)-2-hydroxycyclohexyl)-11-oxo-2-(pyridin-4-yl)-11H-pyrido[2,1-b]quinazoline-6-carboxamide $^1$H-RMN (400 MHz, DMSO-d$_6$): δ=11.48 (d, 1H), 9.05 (dd, 1H), 8.69 (m, 4H), 8.44 (dd, 1H), 7.92 (m, 3H), 7.25 (t, 1H), 5.08 (d, 1H), 3.99 (m, 1H), 3.91 (m, 1H), 1.72 (m, 6H), 1.36 (m, 2H).
HPLC-MS: Rt: 4.083 min, m/z: 415.1 (MH$^+$).

Example 35: N-cyclopentyl-2-(4-methylpiperazin-1-yl)-11-oxo-11H-pyrido[2,1-b]quinazoline-6-carboxamide A mixture of 2-bromo-N-cyclopentyl-11-oxo-11H-pyrido[2,1-b]quinazoline-6-carboxamide (50 mg, 0.13 mmol), 1-methylpiperazine (0.014 mL, 0.13 mmol), Pd$_2$(dba)$_3$ (6 mg, 0.007 mmol), xantphos (8 mg, 0.013 mmol) and Cs$_2$CO$_3$ (51 mg, 0.16 mmol) in 1,4-dioxane (1.5 mL) was stirred under nitrogen atmosphere at 90° C. for 20 hours. The resulting suspension was partitioned between AcOEt and sat. aq. NaHCO$_3$, extracted, dried over MgSO$_4$, filtered and concentrated followed by filtration and purification through flash column chromatography (DCM:MeOH 90:10). 49% yield.
$^1$H-RMN (400 MHz, DMSO-d$_6$): δ=11.06 (d, 1H), 8.91 (dd, 1H), 8.45 (dd, 1H), 7.78 (dd, 1H), 7.58 (d, 1H), 7.48 (d, 1H), 7.10 (t, 1H), 4.31 (m, 1H), 3.27 (m, 4H), 2.52 (m, 4H), 2.25 (s, 3H), 1.98 (m, 2H), 1.78 (m, 2H), 1.67 (m, 4H).
HPLC-MS: Rt: 4.631 min, m/z: 406.0 (MH$^+$).

Example 36: N-cyclohexyl-2-(4-methylpiperazin-1-yl)-11-oxo-11H-pyrido[2,1-b]quinazoline-6-carboxamide $^1$H-RMN (400 MHz, DMSO-d$_6$): δ=11.09 (d, 1H), 8.92 (dd, 1H), 8.47 (dd, 1H), 7.79 (dd, 1H), 7.63 (d, 1H), 7.49 (d, 1H), 7.11 (t, 1H), 3.95 (m, 1H), 3.28 (m, 4H), 2.51 (m, 4H), 2.25 (s, 3H), 1.91 (m, 2H), 1.75 (m, 2H), 1.50 (m, 6H).
HPLC-MS: Rt: 4.975 min, m/z: 420.2 (MH$^+$).

Example 37: N-((1S,2R)-2-hydroxycyclohexyl)-2-(4-methylpiperazin-1-yl)-11-oxo-11H-pyrido[2,1-b]quinazoline-6-carboxamide $^1$H-RMN (400 MHz, DMSO-d$_6$): δ=11.46 (d, 1H), 8.94 (dd, 1H), 8.52 (dd, 1H), 7.82 (m, 1H), 7.72 (d, 1H), 7.52 (d, 1H), 7.12 (t, 1H), 5.01 (d, 1H), 3.97 (m, 1H), 3.87 (m, 1H), 3.30 (m, 4H), 2.52 (m, 4H), 2.25 (s, 3H), 1.70 (m, 6H), 1.38 (m, 2H).
HPLC-MS: Rt: 3.992 min, m/z: 436.2 (MH$^+$).

Example 38: N-cyclohexyl-2-morpholino-11-oxo-11H-pyrido[2,1-b]quinazoline-6-carboxamide $^1$H-RMN (400 MHz, DMSO-d$_6$): δ=11.09 (d, 1H), 8.93 (dd, 1H), 8.49 (dd, 1H), 7.80 (dd, 1H), 7.66 (d, 1H), 7.51 (d, 1H), 7.12 (t, 1H), 3.95 (m, 1H), 3.80 (m, 4H), 3.26 (m, 4H), 1.95 (m, 2H), 1.75 (m, 2H), 1.47 (m, 6H).
HPLC-MS: Rt: 5.134 min, m/z: 407.1 (MH$^+$).

---

---

The invention claimed is:
1. A compound of formula (I):

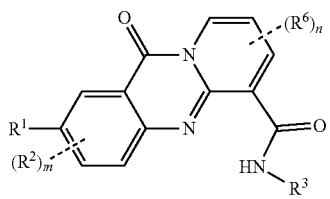

wherein:
R$^1$ represents a group selected from:
a) C$_3$-C$_6$ cycloalkyl optionally substituted by a group selected from halogen atom, linear or branched C$_1$-C$_6$ alkyl and linear or branched C$_1$-C$_4$ alkoxy,
b) phenyl optionally substituted by a group selected from halogen atom and linear or branched C$_1$-C$_6$ alkyl,
c) C$_4$-C$_6$ heterocyclic ring containing 1 or 2 heteroatoms selected from N, O and S and which is optionally substituted by a group selected from halogen atom, linear or branched C$_1$-C$_6$ alkyl and linear or branched C$_1$-C$_4$ alkoxy,
d) fluorine or bromine atom,
e) cyano group,
f) linear or branched C$_1$-C$_3$ alkoxy optionally substituted by 1, 2 or 3 halogen atoms,
g) linear or branched C$_1$-C$_6$ alkyl optionally substituted by 1, 2 or 3 halogen atoms, or
h) —OH,
R$^2$ and R$^6$ independently represent a group selected from:
a) halogen atom,
b) linear or branched C$_1$-C$_6$ alkyl,
c) linear or branched C$_1$-C$_6$ haloalkyl,
d) C$_3$-C$_6$ cycloalkyl optionally substituted by a group selected from halogen atom, linear or branched C$_1$-C$_3$ alkyl and linear or branched C$_1$-C$_2$ alkoxy,
m and n are integers independently selected from 0 and 1,
R$^3$ represents a 5- to 10-membered, saturated, cycle optionally containing 1 or 2 heteroatoms selected from N and O, which is optionally substituted by 1, 2 or 3 groups selected from halogen atoms, linear or branched $C_1$-$C_6$ alkyl, linear or branched $C_1$-$C_6$ alkoxy, —OH and —NR$^4$R$^5$, $R^4$ and $R^5$ represent independently a group selected from hydrogen atom, $C_3$-$C_4$ cycloalkyl group and linear or branched $C_1$-$C_3$ alkyl, with the proviso that the compound of formula:

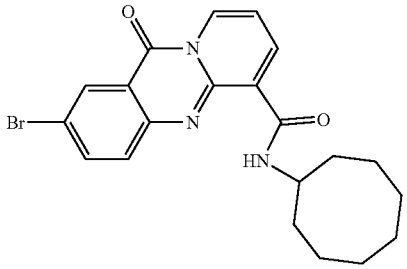 [SMILES: O=C(NC1CCCCCCC1)c1cccn2c(=O)c3cc(Br)ccc3nc12]

is excluded, and pharmaceutically acceptable salts thereof.

2. The compound according to claim 1 wherein $R^1$ represents a group selected from:
$C_3$-$C_6$ cycloalkyl optionally substituted by a group selected from halogen atom, linear or branched $C_1$-$C_6$ alkyl and linear or branched $C_1$-$C_4$ alkoxy,
$C_5$-$C_6$ heterocyclic ring containing 1 or 2 heteroatoms selected from N and O and which is optionally substituted by a group selected from halogen atom, linear or branched $C_1$-$C_6$ alkyl and linear or branched $C_1$-$C_4$ alkoxy, or
linear or branched $C_1$-$C_3$ alkoxy.

3. The compound according to claim 2 wherein $R^1$ represents a group selected from:
$C_3$-$C_4$ cycloalkyl optionally substituted by a group selected from linear or branched $C_1$-$C_6$ alkyl and linear or branched $C_1$-$C_4$ alkoxy,
six-membered heterocyclic ring containing 1 or 2 heteroatoms selected from N and O and which is optionally substituted by a group selected from linear or branched $C_1$-$C_6$ alkyl and linear or branched $C_1$-$C_4$ alkoxy, or
methoxy group.

4. The compound according to claim 3 wherein $R^1$ represents a cyclopropyl group optionally substituted by a group selected from linear or branched $C_1$-$C_6$ alkyl and linear or branched $C_1$-$C_4$ alkoxy.

5. The compound according to claim 1 wherein m and n have a value of 0.

6. The compound according to claim 1 wherein $R^3$ represents a 5- to 10-membered saturated cycle optionally containing one oxygen atom and which is optionally substituted by one group selected from linear or branched $C_1$-$C_6$ alkyl and —OH.

7. The compound according to claim 6 wherein $R^3$ represents a group selected from cyclopentyl and cyclohexyl group optionally substituted by a group selected from linear or branched $C_1$-$C_6$ alkyl and —OH.

8. The compound according to claim 1 wherein $R^1$ represents a group selected from methoxy group, cyclopropyl group optionally substituted by a group selected from linear or branched $C_1$-$C_6$ alkyl and linear or branched $C_1$-$C_4$ alkoxy, and six-membered heterocyclic ring containing 1 or 2 heteroatoms selected from N and O and which is optionally substituted by a group selected from linear or branched $C_1$-$C_6$ alkyl, m and n have a value of 0, and $R^3$ represents a group selected from cyclopentyl and cyclohexyl group optionally substituted by one group selected from linear or branched $C_1$-$C_6$ alkyl and —OH.

9. The compound according to claim 1 wherein $R^1$ represents a group selected from six-membered heterocyclic ring containing 1 or 2 heteroatoms selected from N and O and which is optionally substituted by a group selected from linear or branched $C_1$-$C_6$ alkyl, m and n have a value of 0, and $R^3$ represents a group selected from cyclopentyl and cyclohexyl group optionally substituted by one group selected from linear or branched $C_1$-$C_6$ alkyl and —OH.

10. The compound according to claim 1 wherein $R^1$ represents a cyclopropyl group optionally substituted a group selected from linear or branched $C_1$-$C_3$ alkyl and linear or branched $C_1$-$C_2$ alkoxy, m and n have a value of zero and $R^3$ represents a cyclohexyl group optionally substituted by a group selected from linear or branched $C_1$-$C_3$ alkyl and —OH.

11. The compound according to claim 1 which is one of:
N-cyclohexyl-2-cyclopropyl-11-oxo-11H-pyrido[2,1-b]quinazoline-6-carboxamide
N-cyclopentyl-2-cyclopropyl-11-oxo-11H-pyrido[2,1-b]quinazoline-6-carboxamide
2-cyclopropyl-N-(1-methylpiperidin-4-yl)-11-oxo-11H-pyrido[2,1-b]quinazoline-6-carboxamide
2-cyclopropyl-11-oxo-N-(tetrahydro-2H-pyran-4-yl)-11H-pyrido[2,1-b]quinazoline-6-carboxamide
2-cyclopropyl-N-(3-methyltetrahydro-2H-pyran-4-yl)-11-oxo-11H-pyrido[2,1-b]quinazoline-6-carboxamide
2-cyclopropyl-N-((1R,4R)-4-hydroxy-4-methylcyclohexyl)-11-oxo-11H-pyrido[2,1-b]quinazoline-6-carboxamide
2-cyclopropyl-N-((1R,4R)-4-hydroxycyclohexyl)-11-oxo-11H-pyrido[2,1-b]quinazoline-6-carboxamide
2-cyclopropyl-N-(2-hydroxycyclohexyl)-11-oxo-11H-pyrido[2,1-b]quinazoline-6-carboxamide
2-cyclopropyl-N-((1R,2R)-2-hydroxycyclohexyl)-11-oxo-11H-pyrido[2,1-b]quinazoline-6-carboxamide
2-cyclopropyl-N-((1S,2R)-2-hydroxycyclohexyl)-11-oxo-11H-pyrido[2,1-b]quinazoline-6-carboxamide
2-cyclopropyl-N-((1R,2S)-2-hydroxycyclohexyl)-11-oxo-11H-pyrido[2,1-b]quinazoline-6-carboxamide
2-cyclopropyl-N-((1S,2S)-2-hydroxycyclohexyl)-11-oxo-11H-pyrido[2,1-b]quinazoline-6-carboxamide
N-((1R,4R)-4-aminocyclohexyl)-2-cyclopropyl-11-oxo-11H-pyrido[2,1-b]quinazoline-6-carboxamide
2-cyclopropyl-11-oxo-N-(tetrahydrofuran-3-yl)-11H-pyrido[2,1-b]quinazoline-6-carboxamide
2-cyclopropyl-N-(4,4-difluorocyclohexyl)-11-oxo-11H-pyrido[2,1-b]quinazoline-6-carboxamide
N-cyclohexyl-2-cyclopropyl-8-methyl-11-oxo-11H-pyrido[2,1-b]quinazoline-6-carboxamide
N-(4,4-difluorocyclohexyl)-2-fluoro-8-methyl-11-oxo-11H-pyrido[2,1-b]quinazoline-6-carboxamide
N-cyclopentyl-2-hydroxy-11-oxo-11H-pyrido[2,1-b]quinazoline-6-carboxamide
N-cyclohexyl-2-hydroxy-11-oxo-11H-pyrido[2,1-b]quinazoline-6-carboxamide
N-cyclohexyl-2-methoxy-11-oxo-11H-pyrido[2,1-b]quinazoline-6-carboxamide
N-cyclohexyl-11-oxo-2-(trifluoromethoxy)-11H-pyrido[2,1-b]quinazoline-6-carboxamide
N-cyclohexyl-2-methyl-11-oxo-11H-pyrido[2,1-b]quinazoline-6-carboxamide N-cyclohexyl-11-oxo-2-(trifluoromethyl)-11H-pyrido[2,1-b]quinazoline-6-carboxamide
N-cyclohexyl-2-fluoro-11-oxo-11H-pyrido[2,1-b]quinazoline-6-carboxamide
2-bromo-N-cyclopentyl-11-oxo-11H-pyrido[2,1-b]quinazoline-6-carboxamide
2-bromo-N-cyclohexyl-11-oxo-11H-pyrido[2,1-b]quinazoline-6-carboxamide
2-bromo-N-((1S,2R)-2-hydroxycyclohexyl)-11-oxo-11H-pyrido[2,1-b]quinazoline-6-carboxamide
N-cyclohexyl-11-oxo-2-phenyl-11H-pyrido[2,1-b]quinazoline-6-carboxamide
N-cyclohexyl-2-(4-fluorophenyl)-11-oxo-11H-pyrido[2,1-b]quinazoline-6-carboxamide
N-cyclohexyl-11-oxo-2-(thiophen-2-yl)-11H-pyrido[2,1-b]quinazoline-6-carboxamide
2-cyano-N-cyclohexyl-11-oxo-11H-pyrido[2,1-b]quinazoline-6-carboxamide
N-cyclopentyl-11-oxo-2-(pyridin-4-yl)-11H-pyrido[2,1-b]quinazoline-6-carboxamide
N-cyclohexyl-11-oxo-2-(pyridin-4-yl)-11H-pyrido[2,1-b]quinazoline-6-carboxamide
N-((1S,2R)-2-hydroxycyclohexyl)-11-oxo-2-(pyridin-4-yl)-11H-pyrido[2,1-b]quinazoline-6-carboxamide
N-cyclopentyl-2-(4-methylpiperazin-1-yl)-11-oxo-11H-pyrido[2,1-b]quinazoline-6-carboxamide
N-cyclohexyl-2-(4-methylpiperazin-1-yl)-11-oxo-11H-pyrido[2,1-b]quinazoline-6-carboxamide
N-((1S,2R)-2-hydroxycyclohexyl)-2-(4-methylpiperazin-1-yl)-11-oxo-11H-pyrido[2,1-b]quinazoline-6-carboxamide
N-cyclohexyl-2-morpholino-11-oxo-11H-pyrido[2,1-b]quinazoline-6-carboxamide.

12. A method for the treatment of a disease or pathological condition that can be ameliorated by inhibition of at least one enzyme kinase selected from the group consisting of ARK5, JAK3 and TYK2, wherein the disease is selected from the group consisting of: autoimmune diseases selected from psoriasis, atopic dermatitis, rheumatoid arthritis, multiple sclerosis, alopecia areata, and lupus; inflammatory bowel diseases selected from ulcerative colitis and Crohn's disease; cancer selected from blood cancer, gastric cancer, colon cancer, colorectal cancer, liver cancer, lung cancer, pancreatic cancer, breast cancer, and other solid tumours and others diseases selected from asthma, chronic obstructive pulmonary disease (COPD), transplant rejection, haematological disease, uveitis, dry eye, and allergic conjunctivitis, said method comprising administering a compound according to claim 1 to a subject in need of said treatment.

13. A pharmaceutical composition comprising a compound as defined in claim 1 and a pharmaceutically acceptable diluent or carrier.

14. A pharmaceutical composition according to claim 13 further comprising a therapeutically effective amount of a therapeutic agent selected from an agent useful for the treatment of: autoimmune diseases selected from psoriasis, atopic dermatitis, rheumatoid arthritis, multiple sclerosis, alopecia areata, and lupus; inflammatory bowel diseases selected from ulcerative colitis and Crohn's disease; cancer selected from blood cancer, gastric cancer, colon cancer, colorectal cancer, liver cancer, lung cancer, pancreatic cancer, breast cancer, and other solid tumours; and others diseases selected from asthma, chronic obstructive pulmonary disease (COPD), transplant rejection, haematological disease, uveitis, dry eye and allergic conjunctivitis.

15. A combination product comprising a compound according to claim 1 and at least a therapeutic agent selected from an agent useful for the treatment of autoimmune diseases selected from psoriasis, atopic dermatitis, rheumatoid arthritis, multiple sclerosis, alopecia areata, and lupus; inflammatory bowel diseases selected from ulcerative colitis and Crohn's disease; cancer selected from blood cancer, gastric cancer, colon cancer, colorectal cancer, liver cancer, lung cancer, pancreatic cancer, breast cancer, and other solid tumours; and others diseases selected from asthma, chronic obstructive pulmonary disease (COPD), transplant rejection, haematological disease, uveitis, dry eye and allergic conjunctivitis.

* * * * *

SEQUENCE LISTING

<160> NUMBER OF SEQ ID NOS: 3

<210> SEQ ID NO 1
<211> LENGTH: 13
<212> TYPE: PRT
<213> ORGANISM: Artificial Sequence
<220> FEATURE:
<223> OTHER INFORMATION: Synthetic Construct

<400> SEQUENCE: 1

Lys Lys Ser Arg Gly Asp Tyr Met Thr Met Gln Ile Gly
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic Construct

<400> SEQUENCE: 2

Glu Glu Pro Leu Tyr Trp Ser Phe Pro Ala Lys Lys Lys
1               5                   10

<210> SEQ ID NO 3
<211> LENGTH: 23
<212> TYPE: PRT
<213> ORGANISM: Artificial Sequence
<220> FEATURE:
<223> OTHER INFORMATION: Synthetic Construct

<400> SEQUENCE: 3

Lys Lys Lys Val Ser Arg Ser Gly Leu Tyr Arg Ser Pro Ser Met Pro
1               5                   10                  15

Glu Asn Leu Asn Arg Pro Arg
            20